United States Patent
Burger et al.

(10) Patent No.: US 8,735,424 B2
(45) Date of Patent: May 27, 2014

(54) BICYCLIC KINASE INHIBITORS

(75) Inventors: Matthew Burger, Emeryville, CA (US); Mika Lindvall, Emeryville, CA (US)

(73) Assignee: Novartis AG, Basel (CH)

( * ) Notice: Subject to any disclaimer, the term of this patent is extended or adjusted under 35 U.S.C. 154(b) by 336 days.

(21) Appl. No.: 13/060,971

(22) PCT Filed: Aug. 31, 2009

(86) PCT No.: PCT/EP2009/061182
§ 371 (c)(1),
(2), (4) Date: Mar. 25, 2011

(87) PCT Pub. No.: WO2010/026121
PCT Pub. Date: Mar. 11, 2010

(65) Prior Publication Data
US 2011/0195980 A1    Aug. 11, 2011

Related U.S. Application Data

(60) Provisional application No. 61/093,669, filed on Sep. 2, 2008.

(51) Int. Cl.
*C07D 401/04*    (2006.01)
*A61K 31/47*    (2006.01)

(52) U.S. Cl.
USPC ........... 514/300; 514/313; 514/314; 544/125; 544/159

(58) Field of Classification Search
USPC .................. 546/125, 159; 514/300, 313, 314
See application file for complete search history.

(56) References Cited

U.S. PATENT DOCUMENTS

| | | | |
|---|---|---|---|
| 4,017,500 A | 4/1977 | Mayer et al. | |
| 4,965,265 A | 10/1990 | Heinemann | |
| 5,100,900 A | 3/1992 | Stoltefuss et al. | |
| 5,204,472 A | 4/1993 | Stoltefuss | |
| 5,866,572 A * | 2/1999 | Barker et al. | 514/234.5 |
| 6,391,874 B1 * | 5/2002 | Cockerill et al. | 514/233.5 |
| 6,649,620 B2 * | 11/2003 | Collis et al. | 514/266.22 |
| 2006/0009460 A1 | 1/2006 | Dickson, Jr. et al. | |
| 2006/0167000 A1 | 7/2006 | Barnham et al. | |
| 2006/0276450 A1 | 12/2006 | Trotter et al. | |

FOREIGN PATENT DOCUMENTS

| | | | |
|---|---|---|---|
| EP | 837063 | * | 4/1998 |
| JP | 2006-219453 | | 8/2006 |
| WO | 97/30034 | | 8/1997 |
| WO | 2005/030130 | | 4/2005 |
| WO | 2005/120509 | | 12/2005 |
| WO | WO 2006/135993 | | 12/2006 |
| WO | WO 2008/009078 | | 1/2008 |
| WO | WO 2008/144464 | | 11/2008 |

OTHER PUBLICATIONS

Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, pp. 1004-1010, 1996.*
Traxler, Protein Tyrosine Kinase Inhibitors in Cancer Treatment, Exp. Opin. Ther. Patents, 7(6):571-588 (1997).*
Andina et al., Proviral Integration site for Maloney murine leukemia virus 1, J. Allergy Clin. Immunol. vol. 123, No. 3, pp. 603-611, 2009.*
Godard et al., CAPLUS Abstract 120:323013 (1994).*
Godard et al., CAPLUS Abstract 121:35951 (1994).*
Boger et al., CAPLUS Abstract 120:106610 (1994).*
Thummel et al., CAPLUS Abstract 118:191510 (1993).*
Giorgi-Renault et al., CAPLUS Abstract 112:35800 (1990).*
Boger et al., CAPLUS Abstract 107:175748 (1987).*
Boger et al., CAPLUS Abstract 104:129685 (1986).*
Hibino et al., CAPLUS Abstract 86:72389 (1977).*
Lane et al., CAPLUS Abstract 51:12967 (1957).*
Pfeiffer et al., CAPLUS Abstract 65:99341 (1966).*
Rao et al., CAPLUS Abstract 92:58578 (1980).*
Rao, Koppala V., CAPLUS Abstract 87:184343 (1977).*
Rao, Koppala v., CAPLUS Abstract 83:178775 (1975).*
Rao et al., CAPLUS Abstract 59:62097 (1963).*
Marc Kimber et al., "Synthesis of ABC Analogues of the Antiitumour Antibiotic Streptonigrin" *Tetrahedron* 56:3575-3581, 2000.

* cited by examiner

*Primary Examiner* — Deepak Rao
(74) *Attorney, Agent, or Firm* — Michael G. Smith

(57) ABSTRACT

New compounds, compositions and methods of inhibition of Provirus Integration of Maloney Kinase (PIM kinase) activity associated with tumorigenesis in a human or animal subject are provided. In certain embodiments, the compounds and compositions are effective to inhibit the activity of at least one PIM kinase. The new compounds and compositions may be used either alone or in combination with at least one additional agent for the treatment of a serine/threonine kinase- or receptor tyrosine kinase-mediated disorder, such as cancer.

17 Claims, No Drawings

BICYCLIC KINASE INHIBITORS

CROSS-REFERENCE TO RELATED APPLICATION

This application is a U.S. National Phase filing of International Application No. PCT/EP2009/061182, filed Aug. 31, 2009, and claims the benefit under 35 U.S.C. §119(e) to U.S. provisional application Ser. No. 61/093,669, filed on Sep. 2, 2008, which is incorporated herein in its entirety by reference.

FIELD OF THE INVENTION

The present invention relates to new compounds and their tautomers and stereoisomers, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND

Infection with the Maloney retrovirus and genome integration in the host cell genome results in development of lymphomas in mice. Provirus Integration of Maloney Kinase (PIM-Kinase) was identified as one of the frequent proto-oncogenes capable of being transcriptionally activated by this retrovirus integration event (Cuypers H T et al., "Murine leukemia virus-induced T-cell lymphomagenesis: integration of proviruses in a distinct chromosomal region," *Cell* 37(1): 141-50 (1984); Selten G, et al., "Proviral activation of the putative oncogene Pim-1 in MuLV induced T-cell lymphomas" *EMBO J* 4(7):1793-8 (1985)), thus establishing a correlation between over-expression of this kinase and its oncogenic potential. Sequence homology analysis demonstrated that there are 3 highly homologous Pim-Kinases (Pim1, 2 & 3), Pim1 being the proto-oncogene originally identified by retrovirus integration. Furthermore, transgenic mice over-expressing Pim1 or Pim2 show increased incidence of T-cell lymphomas (Breuer M et al., "Very high frequency of lymphoma induction by a chemical carcinogen in pim-1 transgenic mice" *Nature* 340(6228):61-3 (1989)), while over-expression in conjunction with c-myc is associated with incidence of B-cell lymphomas (Verbeek S et al., "Mice bearing the E mu-myc and E mu-pim-1 transgenes develop pre-B-cell leukemia prenatally" *Mol Cell Biol* 11(2):1176-9 (1991)). Thus, these animal models establish a strong correlation between Pim over-expression and oncogenesis in hematopoietic malignancies. In addition to these animal models, Pim over-expression has been reported in many other human malignancies. Pim1, 2 & 3 over-expression is frequently observed in many hematopoietic malignancies (Amson R et al., "The human protooncogene product p33pim is expressed during fetal hematopoiesis and in diverse leukemias," *PNAS USA* 86(22):8857-61 (1989); Cohen A M et al., "Increased expression of the hPim-2 gene in human chronic lymphocytic leukemia and non-Hodgkin lymphoma," *Leuk Lymph* 45(5):951-5 (2004), Huttmann A et al., "Gene expression signatures separate B-cell chronic lymphocytic leukaemia prognostic subgroups defined by ZAP-70 and CD38 expression status," *Leukemia* 20:1774-1782 (2006)) and in prostate cancer (Dhanasekaran S M, et al., "Delineation of prognostic biomarkers in prostate cancer," *Nature* 412(6849): 822-6 (2001); Cibull T L, et al., "Overexpression of Pim-1 during progression of prostatic adenocarcinoma," *J Clin Pathol* 59(3):285-8 (2006)), while over-expression of Pim3 is frequently observed in hepatocellular carcinoma (Fujii C, et al., "Aberrant expression of serine/threonine kinase Pim-3 in hepatocellular carcinoma development and its role in the proliferation of human hepatoma cell lines," *Int J Cancer* 114:209-218 (2005)) and pancreatic cancer (Li Y Y et al., "Pim-3, a proto-oncogene with serine/threonine kinase activity, is aberrantly expressed in human pancreatic cancer and phosphorylates bad to block bad-mediated apoptosis in human pancreatic cancer cell lines," *Cancer Res* 66(13):6741-7 (2006)).

Pim1, 2 & 3 are Serine/Threonine kinases that normally function in survival and proliferation of hematopoietic cells in response to growth factors and cytokines. Cytokines signaling through the Jak/Stat pathway leads to activation of transcription of the Pim genes and synthesis of the proteins. No further post-translational modifications are required for the Kinase Pim activity. Thus, signaling down stream is primarily controlled at the transcriptional/translational and protein turnover level. Substrates for Pim kinases include regulators of apoptosis such as the Bcl-2 family member BAD (Aho T et al., "Pim-1 kinase promotes inactivation of the pro-apoptotic Bad protein by phosphorylating it on the Ser112 gatekeeper site: *FEBS Letters* 571: 43-49 (2004)), cell cycle regulators such as p21$^{WFA1/CIP1}$ (Wang Z, et al., "Phosphorylation of the cell cycle inhibitor p21Cip1/WAF1 by Pim-1 kinase," *Biochim Biophys Acta* 1593:45-55 (2002)), CDC25A (1999), C-TAK (Bachmann M et al., "The Oncogenic Serine/Threonine Kinase Pim-1 Phosphorylates and Inhibits the Activity of Cdc25C-associated Kinase 1 (C-TAK1). A novel role for Pim-1 at the G2/M cell cycle checkpoint," *J Biol Chem* 179:48319-48328 (2004)) and NuMA (Bhattacharya N, et al., "Pim-1 associates with protein complexes necessary for mitosis," *Chromosoma* 111(2): 80-95 (2002)) and the protein synthesis regulator 4EBP1 (Hammerman P S et al., "Pim and Akt oncogenes are independent regulators of hematopoietic cell growth and survival," *Blood* 105(11):4477-83 (2005)). The effects of Pim(s) in these regulators are consistent with a role in protection from apoptosis and promotion of cell proliferation and growth. Thus, over-expression of Pim(s) in cancer is thought to play a role in promoting survival and proliferation of cancer cells and, therefore, their inhibitions should be an effective way of treating cancers on which they are over-expressed. In fact several reports indicate that knocking down expression of Pim(s) with siRNA results in inhibition of proliferation and cell death (Dai J M, et al., "Antisense oligodeoxynucleotides targeting the serine/threonine kinase Pim-2 inhibited proliferation of DU-145 cells," *Acta Pharmacol Sin* 26(3):364-8 (2005); Fujii et al. 2005; Li et al. 2006). Furthermore, mutational activation of several well know oncogenes in hematopoietic malignancies are thought exert its effects at least in part through Pim(s). For example, targeted down regulation of pim expression impairs survival of hematopoietic cells transformed by Flt3 and BCR/ABL (Adam et al. 2006). Thus, inhibitors to Pim1, 2 &3 would be useful in the treatment of these malignancies. In addition to a potential role in cancer treatment and myeloproliferative diseases, such inhibitor could be useful to control expansion of immune cells in other pathologic condition such as autoimmune diseases, allergic reactions and in organ transplantation rejection syndromes. This notion is supported by the findings that differentiation of Th1 Helper T-cells by IL-12 and IFN-α, results in induction of expression of both Pim1 &2 (Aho T et al., "Expression of human Pim family genes is selectively up-regulated by cytokines promoting T helper type 1, but not T helper type 2, cell differentiation," *Immunology* 116: 82-88 (2005)). Moreover, Pim(s) expression is inhibited in both cell types by the immunosuppressive TGF-β (Aho et al. 2005). These results suggest that Pim kinases are involved in the early differentiation process of Helper T-cells, which coordinate the immunological responses in autoimmune diseases, allergic reaction and tissue transplant rejection.

A continuing need exists for compounds that inhibit the proliferation of capillaries, inhibit the growth of tumors, treat cancer, modulate cell cycle arrest, and/or inhibit molecules such as Pim1, Pim2 and Pim3, and pharmaceutical formulations and medicaments that contain such compounds. A need also exists for methods of administering such compounds, pharmaceutical formulations, and medicaments to patients or subjects in need thereof.

SUMMARY

The present invention provides compounds of Formula I:

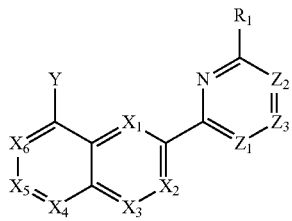

I their stereoisomers, tautomers, and pharmaceutically acceptable salts thereof, wherein, $X_1, X_2, X_3, X_4, X_5$, and $X_6$ are independently selected from $CR_2$ and N, provided that at least one but not more than three of $X_1, X_2, X_3, X_4, X_5$, and $X_6$ are N;

Y is selected from a group consisting of amino, alkoxy, aryl, heteroaryl, partially unsaturated cycloalkyl, cycloalkyl, and heterocycloalkyl, wherein each member of said group is substituted with up to four substituents;

$Z_1, Z_2$, and $Z_3$ are independently selected from $CR_{12}$ and N, provided that not more than two of $Z_1, Z_2$, and $Z_3$ can be N;

$R_1$ selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, aminosulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cyclo alkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

In some embodiments, compounds of Formula I, or a stereoisomer, tautomer, or pharmaceutically acceptable salt thereof are provided wherein not more than two of $X_1, X_2$, and $X_3$ are N, and not more than two of $X_4, X_5$ and $X_6$ are nitrogen. In other embodiments, compounds of Formula I are provided wherein $X_2$, and $X_4$ are N, and $X_1, X_3, X_5$, and $X_6$ are $CR_2$; or wherein $X_4$ is N and $X_1, X_2, X_3, X_5$, and $X_6$ are $CR_2$. In yet other embodiments, new compounds of Formula I are provided wherein $Z_1$ is N or $CR_{12}$, and $Z_2$ and $Z_3$ are $CR_{12}$; or wherein $Z_1$ and $Z_2$ are N or $CR_{12}$, and $Z_3$ is $CR_{12}$.

Another embodiment provides compounds of Formula II:

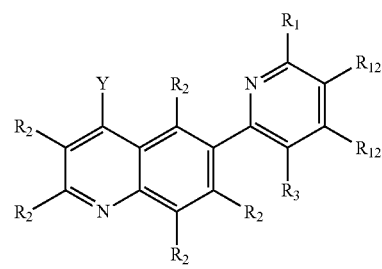

II or a stereoisomer, tautomer, or pharmaceutically acceptable salt thereof, wherein:
wherein, Y is selected from a group consisting of substituted or unsubstituted amino, cyclohexyl, cyclohexenyl, piperidinyl, and piperazinyl;

$R_1$ is selected from the group consisting of unsubstituted and substituted aryl, heteroaryl, alkyl, cycloalkyl, hydrogen, and halo;

$R_3$ is selected from hydrogen, halo, CN, $NH_2$, $NHR_4$, $C_{1-4}$ alkyl, and $C_{3-4}$ cycloalkyl;

$R_2$ and $R_{12}$ independently at each occurrence are selected from the group consisting of hydrogen, halo, hydroxyl, nitro, amino, cyano, $SO_3H$, substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_4$ is selected from the group consisting of hydrogen, carboxy, and substituted or unsubstituted alkyl, cycloalkyl, heterocycloalkyl, aryl and heteroaryl.

Yet another embodiment provides compounds of Formula III:

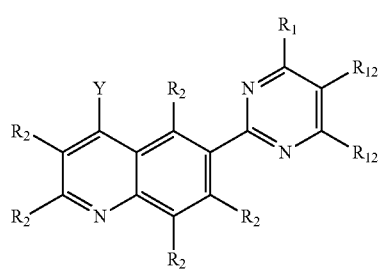

III or a stereoisomer, tautomer, or pharmaceutically acceptable salt thereof, wherein:

Y is selected from the group consisting of substituted or unsubstituted amino, cyclohexyl, cyclohexenyl, piperidinyl, and piperazinyl;

$R_1$ is selected from the group consisting of unsubstituted and substituted aryl, heteroaryl, alkyl, cycloalkyl, hydrogen and halo; and $R_2$ and $R_{12}$ independently at each occurrence are selected from the group consisting of hydrogen, halo, hydroxyl, nitro, amino, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

Yet another embodiment provides compounds of Formula IV:

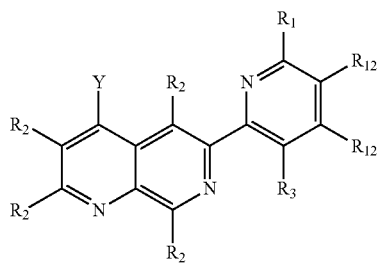

or a stereoisomer, tautomer, or pharmaceutically acceptable salt thereof, wherein, Y is selected from a group consisting of substituted or unsubstituted amino, cyclohexyl, cyclohexenyl, piperidinyl, and piperazinyl;

$R_1$ is selected from the group consisting of unsubstituted and substituted aryl, heteroaryl, alkyl, cycloalkyl, hydrogen and halo;

$R_3$ is selected from hydrogen, halo, CN, $NH_2$, $NHR_4$, $C_{1-4}$ alkyl and $C_{3-4}$ cycloalkyl;

each $R_2$ and $R_{12}$ independently at each occurrence is selected from the group consisting of hydrogen, halo, hydroxyl, nitro, amino, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_4$ is selected from the group consisting of hydrogen, carboxy, and substituted or unsubstituted alkyl, cycloalkyl, heterocycloalkyl, aryl and heteroaryl.

In other embodiments, are provided compounds of Formula I-IV, wherein Y is selected from a group consisting of piperidinyl, piperazinyl, cyclohexyl, pyridyl, pyrimidyl, and pyrazinyl, wherein each member of the group is substituted with up to four substituents. In a preferred embodiment, Y is substituted piperidinyl or cyclohexyl.

In yet other embodiments are provided compounds of Formulas I-IV, wherein $R_{12}$ is selected from amino, hydrogen or halo.

In other aspects of the present invention are provided methods for treating Provirus Integration of Maloney Kinase (PIM Kinase) related disorders in a human or animal subject in need of such treatment comprising administering to said subject an amount of a compound of Formula I, II, III, or IV effective to inhibit PIM activity in the subject.

In other aspects, the present invention provides methods for treating PIM related disorders in a human or animal subject in need of such treatment comprising administering to said subject an amount of a compound of Formula I, II, III or IV effective to reduce or prevent tumor growth in the subject.

In yet other aspects, the present invention provides methods for treating PIM related disorders in a human or animal subject in need of such treatment comprising administering to said subject an amount of a compound of Formula I, II, III or IV effective to reduce or prevent tumor growth in the subject in combination with at least one additional agent for the treatment of cancer.

In yet other aspects, the present invention provides therapeutic compositions comprising at least one compound of Formula I, II, III or IV in combination with one or more additional agents for the treatment of cancer, as are commonly employed in cancer therapy. Yet another aspect provides a pharmaceutical composition further comprising an additional agent for the treatment of cancer, wherein preferably the additional agent is selected from irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, and trastuzumab.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

The invention further provides compositions, methods of use, and methods of manufacture as described in the detailed description of the invention.

DETAILED DESCRIPTION

The present invention in one embodiment provides compounds of Formula I,

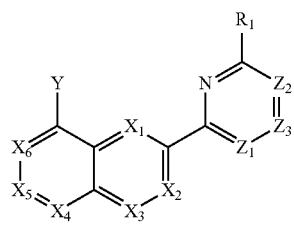

their stereoisomers, tautomers, or pharmaceutically acceptable salts thereof, wherein, $X_1, X_2, X_3, X_4, X_5$, and $X_6$ are independently selected from $CR_2$ and N, provided that at least one but not more than three of $X_1, X_2, X_3, X_4, X_5$, and $X_6$ are N;

Y is selected from a group consisting of amino, alkoxy, aryl, heteroaryl, partially unsaturated cycloalkyl, cycloalkyl, and heterocycloalkyl, wherein each member of said group is substituted with up to four substituents;

$Z_1, Z_2$, and $Z_3$ are independently selected from $CR_{12}$ and N, provided that not more than two of $Z_1, Z_2$, and $Z_3$ can be N;

$R_1$ selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, aminosulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_2$ and $R_{12}$ independently at each occurrence are selected from the group consisting of hydrogen, halo, hydroxyl, nitro, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

In a preferred embodiment are provided compounds of Formula I, or a stereoisomer, tautomer, or pharmaceutically acceptable salt thereof, wherein not more than two of $X_1$, $X_2$, and $X_3$ are N, and not more than two of $X_4$, $X_5$ and $X_6$ are nitrogen. In other embodiments, compounds of Formula I are provided wherein $X_2$, and $X_4$ are N, and $X_1$, $X_3$, $X_5$, and $X_6$ are $CR_2$; or wherein $X_4$ is N and $X_1$, $X_2$, $X_3$, $X_5$, and $X_6$ are $CR_2$. In yet other embodiments, new compounds of Formula I are provided wherein $Z_1$ is N or $CR_{12}$, and $Z_2$ and $Z_3$ are $CR_{12}$; or wherein $Z_1$ and $Z_2$ are N or $CR_{12}$, and $Z_3$ is $CR_{12}$.

Another embodiment provides compounds of Formula II:

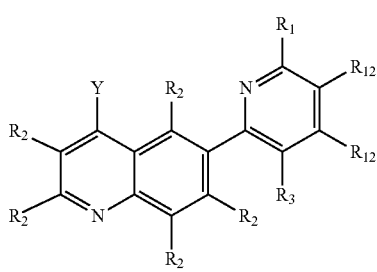

or a stereoisomer, tautomer, or pharmaceutically acceptable salt thereof, wherein:

Y is selected from a group consisting of substituted or unsubstituted amino, cyclohexyl, cyclohexenyl, piperidinyl, and piperazinyl;

$R_1$ is selected from the group consisting of unsubstituted and substituted aryl, heteroaryl, alkyl, cycloalkyl, hydrogen and halo;

$R_3$ is selected form hydrogen, halo, CN, $NH_2$, $NHR_4$, $C_{1-4}$ alkyl and $C_{3-4}$ cycloalkyl;

$R_2$ and $R_{12}$ independently at each occurrence are selected from the group consisting of hydrogen, halo, hydroxyl, nitro, amino, cyano, $SO_3H$ and substituted or unsubstituted alkyl, alkenyl, alkynyl, alkoxy, amino, cycloalkyl, hetero cycloalkyl, aminocarbonyloxy, amino sulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and $R_4$ is selected from the group consisting of hydrogen, carboxy, and substituted or unsubstituted alkyl, cycloalkyl, heterocycloalkyl, aryl and heteroaryl.

Yet another embodiment provides compounds of Formula III:

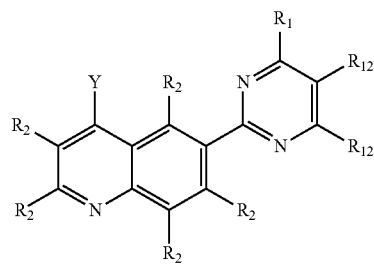

or a stereoisomer, tautomer, or pharmaceutically acceptable salt thereof, wherein, Y is selected from a group consisting of substituted or unsubstituted amino, cyclohexyl, cyclohexenyl, piperidinyl, and piperazinyl;

$R_1$ is selected from the group consisting of unsubstituted and substituted aryl, heteroaryl, alkyl, cycloalkyl, hydrogen and halo; and $R_2$ and $R_{12}$ independently at each occurrence is selected from the group consisting of hydrogen, halo, hydroxyl, nitro, amino, cyano, $SO_3H$ and substituted or unsubstituted alkyl, alkenyl, alkynyl, alkoxy, amino, cycloalkyl, hetero cycloalkyl, aminocarbonyloxy, aminosulfonyl, amino sulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl.

Yet another embodiment provides compounds of Formula IV:

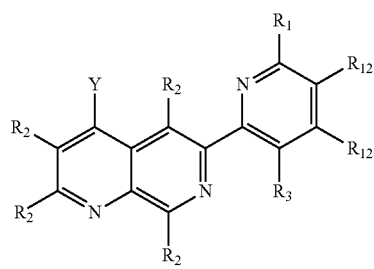

or a stereoisomer, tautomer, or pharmaceutically acceptable salt thereof, wherein:

Y is selected from a group consisting of substituted or unsubstituted amino, cyclohexyl, cyclohexenyl, piperidinyl, and piperazinyl;

$R_1$ is selected from the group consisting of unsubstituted and substituted aryl, heteroaryl, alkyl, cycloalkyl, hydrogen and halo;

$R_3$ is selected from hydrogen, halo, CN, $NH_2$, $NHR_4$, $C_{1-4}$ alkyl and $C_{3-4}$ cycloalkyl;

R$_2$ and R$_{12}$ independently at each occurrence are selected from the group consisting of hydrogen, halo, hydroxyl, nitro, amino, cyano, SO$_3$H and substituted or unsubstituted alkyl, alkenyl, alkynyl, alkoxy, amino, cycloalkyl, hetero cycloalkyl, aminocarbonyloxy, amino sulfonyl, amino sulfonyloxy, amino sulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, cycloalkyl, hetero cycloalkyl, partially saturated cycloalkyl, aryloxy, heteroaryloxy, heterocyclyloxy, cycloalkyloxy, acyl, acylamino and acyloxy, and partially saturated cycloalkyl; and R$_4$ is selected from the group consisting of hydrogen, carboxy, and substituted or unsubstituted alkyl, cycloalkyl, heterocycloalkyl, aryl, and heteroaryl.

In other embodiments, are provided compounds of Formulas I-IV, wherein Y is selected from a group consisting of piperidinyl, piperazinyl, cyclohexyl, pyridyl, pyrimidyl, and pyrazinyl, wherein each member of the group is substituted with up to four substituents. In some embodiments, Y is substituted piperidinyl or cyclohexyl.

In yet other embodiments, are provided of Formulas I-IV, wherein R$_{12}$ is selected from amino, hydrogen, and halo.

In some preferred embodiments, are provided compounds of Formula I, or a stereoisomer, tautomer, or pharmaceutically acceptable salt thereof, selected from the group consisting of (S)-2-(4-(3-aminopiperidin-1-yl)-3-fluoro-1,7-naphthyridin-6-yl)-6-(thiazol-2-yl)pyridin-3-amine, (S)-3-(5-amino-6-(4-(3-aminopiperidin-1-yl)-3-fluoro-1,7-naphthyridin-6-yl)pyridin-2-yl)-4-fluoro-N-isopropylbenzamide, 4-(6-(3-amino-6-(2,6-difluorophenyl)pyridin-2-yl)-1,7-naphthyridin-4-yl)-6-methylpyridin-2-amine, 3-(5-amino-6-(4-(2-amino-6-methylpyridin-4-yl)-1,7-naphthyridin-6-yl)pyridin-2-yl)-4-fluoro-N-isopropylbenzamide, (S)-2-(4-(3-aminopiperidin-1-yl)-1,7-naphthyridin-6-yl)-6-(thiazol-2-yl)pyridin-3-amine, (S)-4-(4-(3-aminopiperidin-1-yl)-1,7-naphthyridin-6-yl)-2-(2-fluorophenyl)pyrimidin-5-amine, (R)-2-(4-(3-aminopiperidin-1-yl)-1,7-naphthyridin-6-yl)-6-(2,6-difluorophenyl)pyridin-3-amine, (R)-3-(5-amino-6-(4-(3-aminopiperidin-1-yl)-1,7-naphthyridin-6-yl)pyridin-2-yl)-4-fluoro-N-isopropylbenzamide, (S)-2-(4-(3-aminopiperidin-1-yl)-1,7-naphthyridin-6-yl)-6-(2,6-difluorophenyl)pyridin-3-amine, (S)-3-(5-amino-6-(4-(3-aminopiperidin-1-yl)-1,7-naphthyridin-6-yl)pyridin-2-yl)-4-fluoro-N-isopropylbenzamide, (S)-2-(4-(3-aminopiperidin-1-yl)-1,7-naphthyridin-6-yl)-6-(2-fluorophenyl)pyridin-3-amine, (S)-3-(5-amino-6-(4-(3-aminopiperidin-1-yl)-1,7-naphthyridin-6-yl)pyridin-2-yl)-4-fluoro-N-phenylbenzamide, (S)-2-(4-(3-aminopiperidin-1-yl)-1,7-naphthyridin-6-yl)-6-(thiophen-2-yl)pyridin-3-amine, (S)-6-(4-(3-aminopiperidin-1-yl)-1,7-naphthyridin-6-yl)-6'-methoxy-2,2'-bipyridin-5-amine, (S)-3-(5-amino-6-(4-(3-aminopiperidin-1-yl)-1,7-naphthyridin-6-yl)pyridin-2-yl)-N-cyclohexyl-4-fluorobenzamide, (S)-3-(5-amino-6-(4-(3-aminopiperidin-1-yl)-1,7-naphthyridin-6-yl)pyridin-2-yl)-4-fluoro-N,N-dimethylbenzamide, (S)-2-(4-(3-aminopiperidin-1-yl)-1,7-naphthyridin-6-yl)-6-(2,4-difluorophenyl)pyridin-3-amine, (S)-2-(4-(3-aminopiperidin-1-yl)-1,7-naphthyridin-6-yl)-6-(2,3-difluorophenyl)pyridin-3-amine, (S)-2-(4-(3-aminopiperidin-1-yl)-1,7-naphthyridin-6-yl)-6-(4-fluorophenyl)pyridin-3-amine, (S)-2-(4-(3-aminopiperidin-1-yl)-1,7-naphthyridin-6-yl)-6-phenylpyridin-3-amine, (S)-3-(5-amino-6-(4-(3-aminopiperidin-1-yl)-1,7-naphthyridin-6-yl)pyridin-2-yl)benzenesulfonamide, (S)-2-(4-(3-aminopiperidin-1-yl)-1,7-naphthyridin-6-yl)-6-(3-(methylsulfonyl)phenyl)pyridin-3-amine, (S)-4-(5-amino-6-(4-(3-aminopiperidin-1-yl)-1,7-naphthyridin-6-yl)pyridin-2-yl)benzenesulfonamide, (S)-2-(4-(3-aminopiperidin-1-yl)-1,7-naphthyridin-6-yl)-6-(4-(methylsulfonyl)phenyl)pyridin-3-amine, (S)-1-(6-(6-(thiazol-2-yl)pyridin-2-yl)-1,7-naphthyridin-4-yl)piperidin-3-amine, (S)-1-(6-(6-(2,6-difluorophenyl)pyridin-2-yl)quinolin-4-yl)piperidin-3-amine, (S)-1-(6-(6-(thiazol-2-yl)pyridin-2-yl)quinolin-4-yl)piperidin-3-amine, (S)-1-(6-(4-(2-fluorophenyl)pyrimidin-2-yl)quinolin-4-yl)piperidin-3-amine, (S)-1-(6-(4-(2,6-difluorophenyl)pyrimidin-2-yl)quinolin-4-yl)piperidin-3-amine, (3S,5R)-5-methyl-1-(6-(6-(thiazol-2-yl)pyridin-2-yl)quinolin-4-yl)piperidin-3-amine, (3R,4R)-1-(6-(6-(2,6-difluorophenyl)pyridin-2-yl)quinolin-4-yl)-4-fluoropiperidin-3-amine, (3R,4R)-4-fluoro-1-(6-(6-(thiazol-2-yl)pyridin-2-yl)quinolin-4-yl)piperidin-3-amine, (3S,5R)-1-(6-(6-(2,6-difluorophenyl)pyridin-2-yl)quinolin-4-yl)-5-methylpiperidin-3-amine, (3R,4R)-3-amino-1-(6-(6-(2,6-difluorophenyl)pyridin-2-yl)quinolin-4-yl)piperidin-4-ol, and (3R,4R)-3-amino-1-(6-(6-(thiazol-2-yl)pyridin-2-yl)quinolin-4-yl)piperidin-4-ol.

In other aspects, the present invention provides methods for treating Provirus Integration of Maloney Kinase (PIM Kinase) related disorders in a human or animal subject in need of such treatment comprising administering to said subject an amount of a compound of Formula I, II, III or IV effective to inhibit PIM activity in the subject.

In other aspects, the present invention provides methods for treating PIM related disorders in a human or animal subject in need of such treatment comprising administering to said subject an amount of a compound of Formula I, II, III or IV effective to reduce or prevent tumor growth in the subject.

In yet other aspects, the present invention provides methods for treating PIM related disorders in a human or animal subject in need of such treatment comprising administering to said subject an amount of a compound of Formula I, II, III or IV effective to reduce or prevent tumor growth in the subject in combination with at least one additional agent for the treatment of cancer.

In yet other aspects, the present invention provides therapeutic compositions comprising at least one compound of Formula I, II, III, or IV in combination with one or more additional agents for the treatment of cancer, as are commonly employed in cancer therapy.

The compounds of the invention are useful in the treatment of cancers, including hematopoietic malignancies, carcinomas (e.g., of the lungs, liver, pancreas, ovaries, thyroid, bladder or colon), melanoma, myeloid disorders (e.g., myeloid leukemia, multiple myeloma and erythroleukemia), adenomas (e.g., villous colon adenoma), sarcomas (e.g., osteosarcoma), autoimmune diseases, allergic reactions and in organ transplantation rejection syndromes.

In another aspect, the present invention relates to methods of inhibiting the activity of at least one kinase selected from the group consisting of Pim1, Pim2 and Pim3, in a subject, or treating a biological condition mediated by at least one of Pim1, Pim2 and Pim3 in a human or animal subject in need of such treatment, comprising administering to the subject at least one compound of Formula I, II, III or IV in an amount effective to inhibit the kinase in the subject. The therapeutic compounds are useful for treating patients with a need for such inhibitors (e.g., those suffering from cancer mediated by abnormal serine/threonine kinase receptor signaling).

The invention further provides compositions, methods of use, and methods of manufacture as described in the detailed description of the invention.

Definitions

"PIM inhibitor" is used herein to refer to a compound that exhibits an $IC_{50}$ with respect to PIM Kinase activity of no more than about 100 μM and more typically not more than about 50 as measured in the PIM depletion assays described hereinbelow.

The phrase "alkyl" refers to $C_{1-10}$ alkyl groups. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched $C_{3-8}$-alkyl groups, including but not limited to, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$, CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and the like. Thus the phrase alkyl groups includes primary alkyl groups, secondary alkyl groups, and tertiary alkyl groups. Preferred alkyl groups include straight and branched chain alkyl groups having 1 to 6 carbon atoms.

The term "alkenyl" refers to alkyl groups as defined above, containing at least one point of unsaturation, ie., wherein two adjacent carbon atoms are attached by a double bond. The term "alkenyl" refers to alkyl groups wherein two adjacent carbon atoms are attached by a triple bond. The term 'alkoxy" refers to groups of the formula —OR, wherein R is alkyl as defined above.

As used herein, the term "halogen" or "halo" refers to chloro, bromo, fluoro, and iodo groups. The term "haloalkyl" refers to an alkyl group as defined above, wherein one or more hydrogen atoms in the alkyl group is replaced by one or more halogen atoms. The term "haloalkyl" thus includes monohalo alkyl, dihalo alkyl, trihalo alkyl, and the like.

"Amino" refers herein to the group —NH$_2$. The term "alkylamino" refers to the group —NRR' where R and R' are each independently selected from hydrogen and alkyl. The term "arylamino" refers herein to the group —NR"R' wherein R" is aryl and R' is hydrogen, alkyl, or an aryl. The term "aralkylamino" refers herein to the group —NRR' where R is aralkyl and R' is hydrogen, alkyl, an aryl, or a aralkyl. The term cyano refers to the group —CN. The term nitro refers to the group —NO$_2$.

The term "alkoxyalkyl" refers to the group -alk$_1$-O-alk$_2$ where alk$_1$ is alkyl or alkenyl, and alk$_2$ is alkyl or alkenyl. The term "aryloxyalkyl" refers to the group -alkyl-O-aryl. The term "aralkoxyalkyl" refers to the group -alkylenyl-O-aralkyl, where aralkyl is a aralkyl.

The term "aminocarbonyl" refers herein to the group —C(O)—NH$_2$. "Substituted aminocarbonyl" refers herein to the group —C(O)—NRR' where R is alkyl and R' is hydrogen or a alkyl. In some embodiments, R and R', together with the N atom to which they are attached can be taken together to form a "heterocycloalkylcarbonyl" group. The term "arylaminocarbonyl" refers herein to the group —C(O)—NRR' where R is an aryl and R' is hydrogen, alkyl or aryl. The term "aralkylaminocarbonyl" refers herein to the group —C(O)—NRR' where R is aralkyl and R' is hydrogen, alkyl, aryl, or aralkyl.

"Aminosulfonyl" refers herein to the group —S(O)$_2$—NH$_2$. "Substituted aminosulfonyl" refers herein to the group —S(O)$_2$—NRR' where R is alkyl and R' is hydrogen or alkyl. The term "aralkylaminosulfonlyaryl" refers herein to the group aryl-S(O)$_2$—NH-aralkyl.

"Carbonyl" refers to the divalent group —C(O)—. "Carboxy" refers to —C(=O)—OH. "Alkoxycarbonyl" refers to ester —C(=O)—OR wherein R is alkyl. "Loweralkoxycarbonyl" refers to ester —C(=O)—OR wherein R is $C_{1-4}$-alkyl. "Cycloalkyloxycarbonyl" refers to —C(=O)—OR wherein R is cycloalkyl.

"Cycloalkyl" refers to a mono- or polycyclic, carbocyclic alkyl substituent. Typical cycloalkyl substituents have from 3 to 8 ring carbon atoms. Carbocycloalkyl groups are cycloalkyl groups in which all ring atoms are carbon atoms. Illustrative examples of cycloalkyl group are cyclohexyl, cyclopentyl, cyclopropyl, cyclobutyl, and the like. When used in connection with cycloalkyl substituents, the term "polycyclic" refers herein to fused and non-fused alkyl cyclic structures. Illustrative examples of a polycyclic cycloalkyl group are octahydro-1H-indene, bicyclo[4.2.0]octane, bicyclo[3.2.0]heptane, spiro[3.3]heptane, and the like. The term partially unsaturated cycloalkyl group refers to a cycloalkyl group as defined above, wherein at least two adjacent carbon atoms of the cycloalkyl group are connected to each other by a double or a triple bond. Illustrative examples of partially unsaturated cycloalkyl groups include cyclopentenyl, cyclopentynyl, cyclohexenyl, cyclohexynyl, and the like.

The term "heterocycle" or "heterocyclic group" or "heterocycloalkyl" as used herein refers to a 4 to 10 membered cyclic ring system wherein at least one but not more than five members of the ring system is a heteroatom selected from nitrogen, oxygen, and sulfur. A preferred heterocyclic group is a 5- or 9-membered cyclic ring system wherein from one to three members of the ring system are heteroatoms selected from the group consisting of nitrogen, oxygen, and sulfur. It should be noted that the nitrogen and sulfur atom contained within the heterocyclic ring systems maybe optionally oxidized as well as optionally quarternized. It is further understood that the term heterocycle, or heterocyclic group, or heterocycle, as used herein can include a single or multiple double or triple bonds. Illustrative examples of the heterocyclic group are piperidinyl, 1,2,3,4-tetrahydropyridine, tetrahydropyran, 3,6-dihydro-2H-pyran, tertahydrofuran, piperidine, and the like.

Heterocyclic moieties can be unsubstituted, monosubstituted, disubstituted, or trisubstituted with substituents independently selected from hydroxy, halo, oxo (C=O), alkylimino (RN=, wherein R is a loweralkyl or loweralkoxy group), amino, alkylamino, dialkylamino, acylaminoalkyl, alkoxy, thioalkoxy, polyalkoxy, alkyl, alkenyl, alkenyl, halo, cyano, nitro, cycloalkyl, or haloalkyl.

The heterocyclic groups may be attached at various positions as will be apparent to those skilled in the organic, and/or medicinal chemistry arts.

Representative heterocyclic moieties include, imidazolyl, pyridyl, piperazinyl, piperidinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

The term "aryl" as used herein, refers to optionally substituted monocyclic and polycyclic aromatic groups having from 5 to 12 membered ring systems. Illustrative examples of aryl groups are phenyl, naphthyl, and the like. The term "heteroaryl" as used herein represents 5 to 12 membered cyclic aromatic structures wherein from 1 to about 6 members are heteroatoms selected from N, O, and S. Illustrative examples of a heteroaryl group are pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

"Optionally substituted" or "substituted" refers to the replacement of one or more hydrogen atoms with a monovalent or divalent radical. Suitable substitution groups include, for example, hydroxy, nitro, amino, imino, cyano, halo, thio, sulfonyl, thioamido, amidino, imidino, oxo, guanidino, sulfonamido, carboxyl, formyl, loweralkyl, halo loweralkyl, loweralkylamino, halo loweralkylamino, loweralkoxy, halo loweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxy, loweralkyl, loweralkoxy, aminocarbonyl, —SR, thioamido, —SO$_3$H, —SO$_2$R or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, or their stereoisomers, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

The compounds of the invention, or their tautomers, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)- or (S)-forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or alkaline earth metal salts of the compounds of Formulas I, II, III or IV. These salts can be prepared in situ during the final isolation and purification of the compounds of Formulas I, II, III or IV, or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

The invention further provides deuterated versions of the above-described compounds. As used herein, "deuterated version" refers to a compound in which at least one hydrogen atom is enriched in the isotope deuterium beyond the natural rate of deuterium occurrence. Typically, the hydrogen atom is enriched to be at least 50% deuterium, frequently at least 75% deuterium, and preferably at least about 90% deuterium. Optionally, more than one hydrogen atom can be replaced by deuterium. For example, a methyl group can be deuterated by replacement of one hydrogen with deuterium (i.e., it can be —CH$_2$D), or it can have all three hydrogen atoms replaced with deuterium (i.e., it can be —CD$_3$). In each case, D signifies that at least 50% of the corresponding H is present as deuterium.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the invention, or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of formula (I) or their tautomers, prodrugs and stereoisomers, as well as the pharmaceutically acceptable salts, esters and prodrugs of any of them, are included within the invention.

The term "cancer" refers to cancer diseases that can be beneficially treated by the inhibition of Pim kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma and erythroleukemia), adenomas (e.g., villous colon adenoma) and sarcomas (e.g., osteosarcoma).

Synthetic Methods

The compounds of the present invention can be obtained through procedures known to one skilled in the art. As depicted in Scheme I, 4-chloro-6-bromoquinoline can be displaced by an amine or organometallic at the chloro to yield a 4-substituted 6-bromoquinoline. Conversion of the bromo into corresponding boronate ester and coupling with substituted heteroarylhalides or triflates can yield, 6 disubstituted quinolines I. If the Het2 in I has a halo or triflate precursor, Het2 can be further modified by standard organometallic or amination methodologies.

Scheme 2 depicts an alternative method to access 4,6 disubstituted quinolines. Chloro displacement of with benzyl alcohol, followed by conversion of the bromo to the corresponding boronate ester and Suzuki reaction with a substituted heteroarylhalide or triflate can yield a 4-benzyloxy 6-substituted quinoline. Benzyl deprotection, followed by triflation to yields II. Reaction of tiflate II under amination or organometallic coupling conditions allows access to 4,6 disubstituted quinolines III.

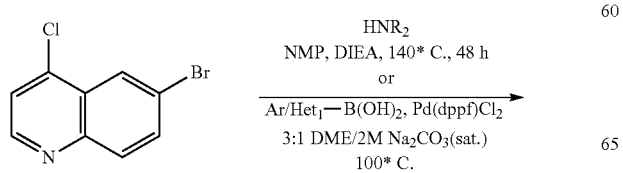

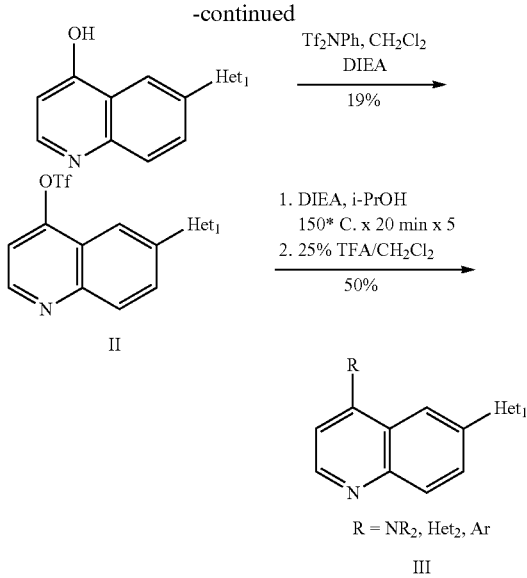

A route to prepare 4-hydroxy 6-chloro 1,7 napthyridine is depicted in Scheme III. Starting with 2-chloro-4-methyl-5-nitropyridine, condensation with dimethylformamidedimethylacetal and subsequent oxidative cleavage yields 2-chloro-5-nitroisonicotinaldehyde. Chemoselective methyl addition to the aldehyde with methyllithium and titaniumtetrachloride at −50° C. followed by oxidation yields 1-(2-chloro-5-nitropyridin-4-yl)ethanone. Nitro reduction with iron in acetic acid, followed by a two step monotosylation yields N-(4-acetyl-6-chloropyridin-3-yl)-4-nitrobenzenesulfonamide. Upon heating with dimethylformamidedimethylacetal and diisopropylethylamine in DMF at 105° C. and subsequent treatment with thiophenol at room temperature, 6-chloro-1,7-naphthyridin-4-ol is obtained IV. Conversion of IV to the corresponding triflate or benzyl ether using standard conditions yields bifunctional intermediates which can be taken through the chemical transformation depicted in Schemes 1 and 2 to yield 4,6 disubstituted 1,7 naphthyridines V.

Scheme 3

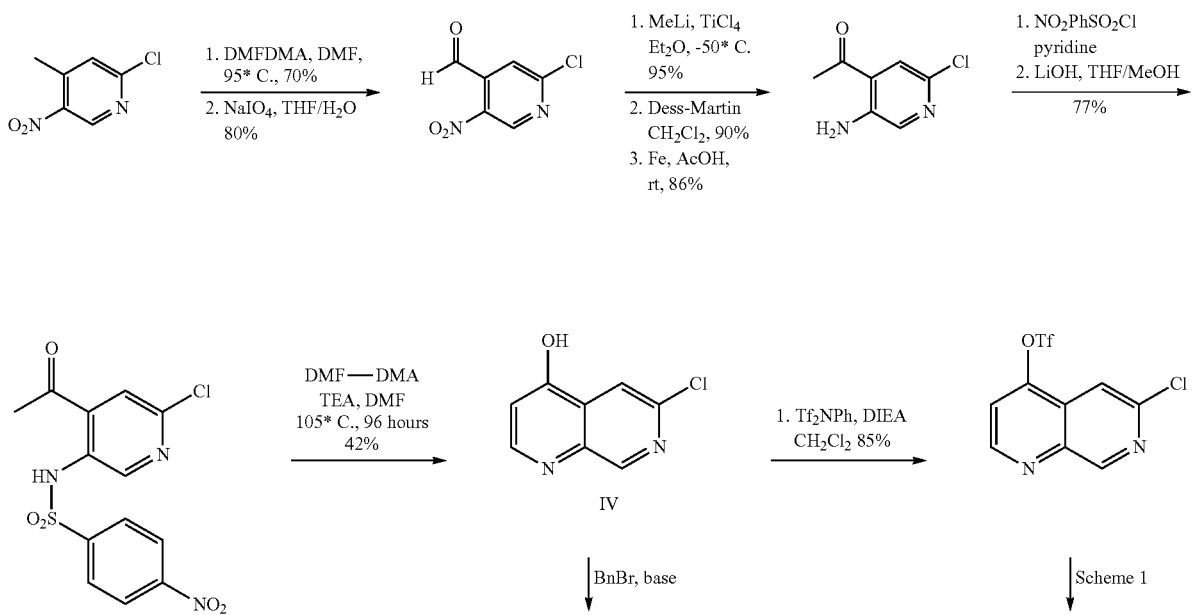

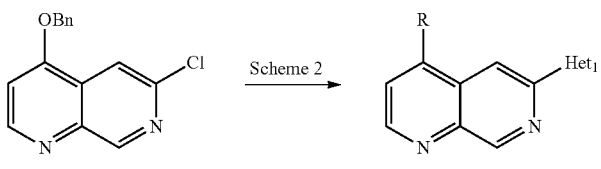

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Pim activity by any of the assays described herein, by other Pim kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

In one embodiment, the invention provides a method of inhibiting Pim1, Pim2 or Pim3 in a human or animal subject. The method includes administering an effective amount of a compound, or a pharmaceutically acceptable salt thereof, of any of the embodiments of compounds of Formula I, II, III or IV to a subject in need thereof.

The present invention will be understood more readily by reference to the following examples, which are provided by way of illustration and are not intended to be limiting of the present invention.

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18 –5μ, 4.6×50 mm, from Alltech (Deerfield, Ill.). A gradient elution was used (flow 2.5 mL/min), typically starting with 5% acetonitrile/ 95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of three LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.), another Waters System (ACQUITY HPLC system and a ZQ 2000 system; Column: ACQUITY HPLC HSS-C18, 1.8 um, 2.1×50 mm; gradient: 5-95% (or 35-95%, or 65-95% or 95-95%) acetonitrile in water with 0.05% TFA over a 1.3 min period; flow rate 1.2 mL/min; molecular weight range 150-850; cone Voltage 20 V; column temperature 50° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

Nuclear magnetic resonance (NMR) analysis was performed on some of the compounds with a Varian 300 MHz NMR (Palo Alto, Calif.). The spectral reference was either TMS or the known chemical shift of the solvent.

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings

| ABBREVIATIONS | |
|---|---|
| DAST | (diethylamino)sulfurtrifluoride |
| DCM | dichloromethane |
| DIEA | diisopropylethylamine |
| DMA | dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| $K_2CO_3$ | Potassium carbonate |
| MeCN | acetonitrile |
| $MgSO_4$ | Magnesium sulfate |
| MeOH | methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$-DCM | Dichloro-(1,2-bis(diphenylphosphino)ethan)-Palladium(II) - dichloromothethane adduct |
| RT or rt | room temperature |
| TDMSCl | tert-butyldimethylsilylchloride |

| ABBREVIATIONS | |
|---|---|
| TEA | triethylamine |
| THF | tetrahydrofuran |

Example 1

Synthesis of (E)-2-(2-chloro-5-nitropyridin-4-yl)-N,N-dimethylethenamine

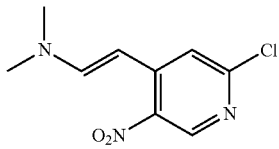

A solution of 2-chloro-4-methyl-5-nitropyridine (1.0 equiv), 25.2 mL dimethylacetal dimethylformamide (2.2 equiv.) in dimethylformamide (0.8 M) was heated at 95° C. for 18 hours. Upon cooling the volatiles were removed in vacuo. The crude material was recrystallized from boiling methanol to yield (E)-2-(2-chloro-5-nitropyridin-4-yl)-N,N-dimethylethenamine (70%) as a red solid. $^1$H NMR (CDCl$_3$): δ 8.80 (s, 1H), 7.32 (d, J=13.2, 1H), 7.25 (s, 1H), 5.95 (d, J=13.2, 1H), 3.02 (bs, 6H).

Synthesis of 2-chloro-5-nitroisonicotinaldehyde

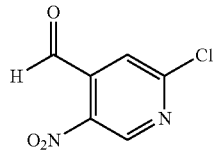 [SMILES: O=Cc1cc(Cl)ncc1[N+](=O)[O-]]

To a solution of (E)-2-(2-chloro-5-nitropyridin-4-yl)-N,N-dimethylethenamine (1.0 equiv) in 1:1 THF/H$_2$O (0.1 M) was added sodium periodate (3.0 equiv) portionwise. The resulting solution was stirred at rt for 6 hours, at which time the white solid was filtered and rinsed with ethyl acetate. The entire filtrate was washed with NaHCO$_{3(sat.)}$, with NaCl$_{(sat.)}$, dried over MgSO$_4$, filtered and concentrated. Purification by column chromatography (20% ethyl acetate/hexanes, R$_f$=0.3) yielded 2-chloro-5-nitroisonicotinaldehyde (71%). $^1$H NMR (CDCl$_3$): δ 10.51 (s, 1H), 9.25 (s, 1H), 7.75 (s, 1H).

Synthesis of 1-(2-chloro-5-nitropyridin-4-yl)ethanol

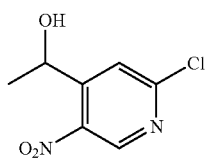

An oven dried 250 mL 3 neck r.b.f. equipped with an internal thermometer was charged with diethyl ether (180 mL) and titanium tetrachloride, 1.0 M in dichloromethane (20.5 mL, 20.5 mmoles) under an Argon atmosphere. The solution was cooled in a CO$_{2(a)}$/acetone −78° C. bath and methyl lithium, 1.6 M in diethyl ether (12.8 mL, 20.5 mmoles) was added via a syringe at a rate such that the internal temperature was </=−50° C. The resultant anion solution was stirred at −50° C. for 1 hour, at which time 2-chloro-5-nitroisonicotinaldehyde (2.54 g, 13.66 mmoles) in diethyl ether (16+4 mL) was added via syringe with the internal temp </=−50° C. After stirring for an additional hour at −50° C., the reaction was poured into H$_2$O (500 mL), and after mixing two light yellow layers formed. Diethyl ether was added (500 mL), the layers were separated, and the organic was washed with H$_2$O (250 mL), with NaCl$_{(sat.)}$ (250 mL), dried over MgSO$_4$, filtered and concentrated yielding 1-(2-chloro-5-nitropyridin-4-yl)ethanol (2.76 g, 100% yield). LCMS (m/z): 203.0 (MH$^+$); LC R$_f$=2.42 min. $^1$H NMR (CDCl$_3$): δ 8.99 (s, 1H), 7.88 (s, 1H), 5.52 (m, 1H), 1.56 (d, J=9.0, 3H).

Synthesis of 1-(2-chloro-5-nitropyridin-4-yl)ethanone

To a solution of 1-(2-chloro-5-nitropyridin-4-yl)ethanol (1.0 equiv.) in dichloromethane (0.1 M) was added Dess-Martin periodinane (1.8 eq.) and the solution was stirred for 16 hours. The solution was poured into ethyl acetate (800 mL), was washed with 1:1 10% Na$_2$S$_2$O$_3$/NaHCO$_{3(sat.)}$ (4×), with NaCl$_{(sat.)}$, dried over MgSO$_4$, filtered and concentrated yielding 1-(2-chloro-5-nitropyridin-4-yl)ethanone (96%) as a yellow solid. LCMS (m/z): 201.0 (MH$^+$); LC R$_f$=2.80 min. $^1$H NMR (CDCl$_3$): δ 9.18 (s, 1H), 7.36 (s, 1H), 2.60 (s, 3H).

Synthesis of 1-(5-amino-2-chloropyridin-4-yl)ethanone

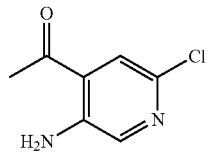

To a solution of 1-(2-chloro-5-nitropyridin-4-yl)ethanone (1.0 equiv.) in acetic acid (0.3 M) was added iron (6.0 equiv.). The solution was vigorously stirred for 4 hours, at which time it was filtered through a celite pad (9 cm×3 inches) eluting with MeOH and then ethyl acetate. The volatiles were removed in vacuo, and the crude material was partitioned between ethyl acetate and Na$_2$CO$_{3(sat.)}$. The organic layer was washed further with Na$_2$CO$_{3(sat.)}$ (3×), with NaCl$_{(sat.)}$, dried over MgSO$_4$, filtered and concentrated yielding 1-(5-amino-2-chloropyridin-4-yl)ethanone (87%). LCMS (m/z):

171.0 (MH⁺); LC R$_t$=2.20 min. ¹H NMR (CDCl₃): δ 9.18 (s, 1H), 7.36 (s, 1H), 2.60 (s, 3H).

Synthesis of N-(4-acetyl-6-chloropyridin-3-yl)-4-nitro-N-(4-nitrophenylsulfonyl)benzenesulfonamide

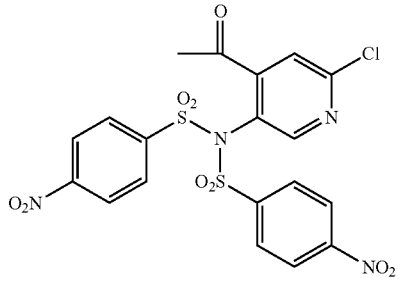 [SMILES: CC(=O)c1cc(Cl)ncc1N(S(=O)(=O)c1ccc([N+](=O)[O-])cc1)S(=O)(=O)c1ccc([N+](=O)[O-])cc1]

To a solution of 1-(5-amino-2-chloropyridin-4-yl)ethanone (1.0 equiv.) in pyridine (0.26 M) was added 4-nitrophenylsulfonylchloride (3.0 equiv.). The resulting amber solution was stirred at rt for 18 hours, at which time it was poured onto ice. The resulting solid was filtered, rinsed with H₂O and pumped on yielding N-(4-acetyl-6-chloropyridin-3-yl)-4-nitro-N-(4-nitrophenylsulfonyl)benzenesulfonamide (88%). LC R$_t$=4.77 min.

Synthesis of N-(4-acetyl-6-chloropyridin-3-yl)-4-nitrobenzenesulfonamide

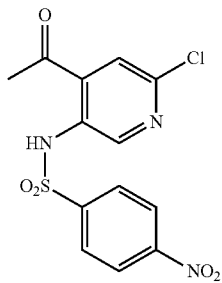 [SMILES: CC(=O)c1cc(Cl)ncc1NS(=O)(=O)c1ccc([N+](=O)[O-])cc1]

To a solution of N-(4-acetyl-6-chloropyridin-3-yl)-4-nitro-N-(4-nitrophenylsulfonyl)benzenesulfonamide (1.0 equiv.) in 2:1 THF/MeOH (0.05 M) was added 1 M LiOH (aq.) (3.1 equiv). The resulting purple solution was stirred at rt for 15 hours, at which time 1 M HCl (3.1 equiv) was added. The volatiles were removed in vacuo and ethyl acetate (700 mL) and H₂O (200 mL) were added. Upon separating the organic was washed with NaHCO₃(sat.) (200 mL), with NaCl(sat.) (200 mL), dried over MgSO₄, filtered and concentrated. Purification by column chromatography (50% ethyl acetate/hexanes with 0.1% AcOH, R$_f$=0.6) yielded N-(4-acetyl-6-chloropyridin-3-yl)-4-nitrobenzenesulfonamide (84%). LCMS (m/z): 356.0 (MH⁺); LC R$_t$=3.81 min. ¹H NMR (CDCl₃): δ 8.89 (s, 1H), 8.32 (m, 2H), 8.06 (m, 2H), 7.62 (s, 1H), 2.60 (s, 3H).

Synthesis of 6-chloro-1,7-naphthyridin-4-ol

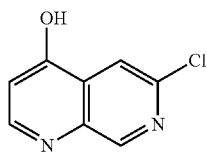 [SMILES: Oc1ccnc2cnc(Cl)cc12]

A solution of N-(4-acetyl-6-chloropyridin-3-yl)-4-nitrobenzenesulfonamide (1.0 equiv.), dimethylformamidedimethylacetal (4.8 equiv.) and DIEA (4.8 equiv.) in DMF (0.15 M) was heated under Ar at 110° C. for 96 hours. Upon cooling, thiophenol (4.9 equiv.) was added and the solution was stirred at rt for 15 hours. The volatiles were removed in vacuo and following silica gel purification (0-1.5-3-5% MeOH/CH₂Cl₂) 6-chloro-1,7-naphthyridin-4-ol was obtained (55%). LC/MS=180.9/182.9 (M+H), LC=1.41 min Synthesis of 6-chloro-1,7-naphthyridin-4-yl trifluoromethanesulfonate

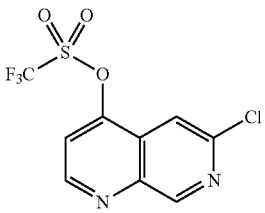 [SMILES: O=S(=O)(Oc1ccnc2cnc(Cl)cc12)C(F)(F)F]

A solution of 6-chloro-1,7-naphthyridin-4-ol (1.0 equiv.), diisopropylethylamine (2.0 equiv.), and 1,1,1-trifluoro-N-phenyl-N-(trifluoromethylsulfonyl)methanesulfonamide (1.5 equiv.) in CH₂Cl₂ was stirred for 16 hours. The solution was partitioned between EtOAc and Na₂CO₃(sat.). Upon separation, the organic layer was washed further with Na₂CO₃(sat.) and NaCl(sat.), dried over MgSO₄, concentrated and purified by silica gel chromatography (10-15% EtOAc/hexanes eluant) to yield 6-chloro-1,7-naphthyridin-4-yl trifluoromethanesulfonate (65%). LC/MS=131.0/315.0 (M+H), LC=4.86 min.

Synthesis of (S)-tert-butyl 1-(6-chloro-1,7-naphthyridin-4-yl)piperidin-3-ylcarbamate

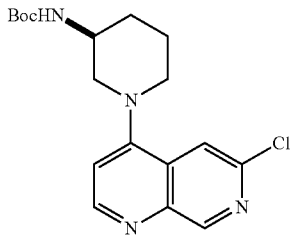 [SMILES: CC(C)(C)OC(=O)N[C@H]1CCCN(c2ccnc3cnc(Cl)cc23)C1]

A solution of 6-chloro-1,7-naphthyridin-4-yl trifluoromethanesulfonate (1.0 equiv.), (S)-tert-butyl piperidin-3-ylcarbamate (1.0 equiv.) and DIEA (1.5 equiv.) in CH₂Cl₂ (0.3 M) was stirred at rt for 120 hours. The solution was partitioned between EtOAc and Na$_2$CO$_{3(sat.)}$. Upon separation, the organic layer was washed with NaCl$_{(sat.)}$, dried over MgSO$_4$, concentrated and purified by silica gel chromatography (EtOAc eluant) to yield (S)-tert-butyl 1-(6-chloro-1,7-naphthyridin-4-yl)piperidin-3-ylcarbamate (61%). LC/MS=363.2 (M+H), LC=2.47 min.

Synthesis of (S)-tert-butyl 1-(6-(4,4,5,5-tetramethyl-1,3,2-dioxaborolan-2-yl)-1,7-naphthyridin-4-yl)piperidin-3-ylcarbamate

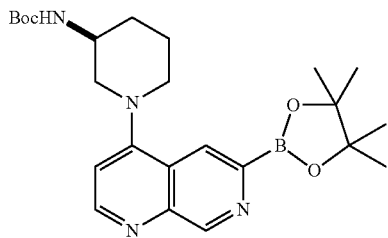

A solution (S)-tert-butyl 1-(6-chloro-1,7-naphthyridin-4-yl)piperidin-3-ylcarbamate (1.0 equiv.), potassium acetate (3.0 equiv.), bis(pinacolato)diboron (2.0 equiv.), tricyclohexylphosphine (0.8 equiv.) and Pd$_2$(dba)$_3$ (0.2 equiv.) in dioxane (0.06 M) was heated at 135° C. in a microwave for 20 minutes. The solution was filtered through a 1 µM HPLC filter, concentrated and pumped to yield (S)-tert-butyl 1-(6-(4,4,5,5-tetramethyl-1,3,2-dioxaborolan-2-yl)-1,7-naphthyridin-4-yl)piperidin-3-yl-carbamate which was used directly. LC/MS=373.1 (M+H of corresponding HetB(OH)$_2$).

Synthesis of (S)-tert-butyl 1-(6-chloro-3-fluoro-1,7-naphthyridin-4-yl)piperidin-3-ylcarbamate

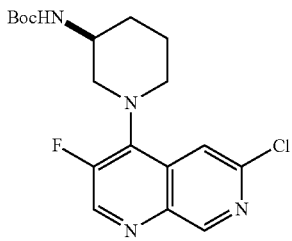 [SMILES: CC(C)(C)OC(=O)N[C@H]1CCCN(c2c(F)cnc3cnc(Cl)cc23)C1]

1-Chloromethyl-4-fluoro-1,4-diazoniabicyclo[2.2.2]octane bis(tetrafluoroborate) (1.0 equiv.) was added to a solution of (S)-tert-butyl 1-(6-chloro-1,7-naphthyridin-4-yl)piperidin-3-ylcarbamate (1.0 equiv.) in MeCN (0.14 M). After stirring for 18 hours, Na$_2$CO$_{3(sat.)}$ was added to quench. The solution was partitioned between EtOAc and Na$_2$CO$_{3(sat.)}$ washed further with NaCl$_{(sat.)}$, dried over MgSO$_4$, concentrated and purified by silica gel chromatography (25-50-100% EtOAc/hexanes w/0.1% DIEA eluant) to yield (S)-tert-butyl 1-(6-chloro-3-fluoro-1,7-naphthyridin-4-yl)piperidin-3-ylcarbamate (15%), as well as recovered (S)-tert-butyl 1-(6-chloro-1,7-naphthyridin-4-yl)piperidin-3-ylcarbamate (55%). LCMS (m/z): 381.1/383.0 (MH$^+$); LC R$_t$=4.20 min.

Synthesis of (S)-tert-butyl 1-(3-fluoro-6-(4,4,5,5-tetramethyl-1,3,2-dioxaborolan-2-yl)-1,7-naphthyridin-4-yl)piperidin-3-ylcarbamate

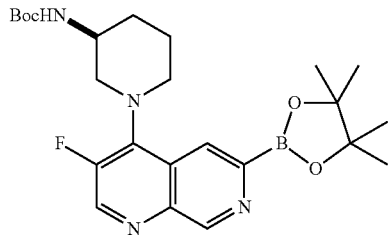 [SMILES: CC(C)(C)OC(=O)N[C@H]1CCCN(c2c(F)cnc3cnc(B4OC(C)(C)C(C)(C)O4)cc23)C1]

A solution (S)-tert-butyl 1-(6-chloro-3-fluoro-1,7-naphthyridin-4-yl)piperidin-3-ylcarbamate (1.0 equiv.), potassium acetate (3.0 equiv.), bis(pinacolato)diboron (2.0 equiv.), tricyclohexylphosphine (0.8 equiv.) and Pd$_2$(dba)$_3$ (0.2 equiv.) in dioxane (0.12 M) was heated at 135° C. in a microwave for 2×15 minutes. The solution was filtered through a 1 µM HPLC filter, concentrated and pumped to yield (S)-tert-butyl 1-(3-fluoro-6-(4,4,5,5-tetramethyl-1,3,2-dioxaborolan-2-yl)-1,7-naphthyridin-4-yl)piperidin-3-yl-carbamate which was used directly. LC/MS=391.2 (M+H of corresponding HetB(OH)$_2$), LC=2.64 min.

Synthesis of 4-chloro-6-methylpyridin-2-amine

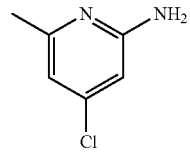

To a 10% aqueous solution of dioxane (0.1 M) was added 4,6-dichloropyridin-2-amine (1.0 equiv.), trimethylboroxine (1.5 equiv.), Pd(PPh$_3$)$_4$ (0.10 equiv.) and K$_2$CO$_3$ (3.0 equiv.). The solution was heated in an oil bath to 120° C. for 18 hrs, cooled to room temperature (not all of starting material was consumed), extracted with EtOAc, dried with Na$_2$SO$_4$, and concentrated. The crude material was purified via SiO$_2$ column chromatography eluting with 5% MeOH/DCM to yield 4-chloro-6-methylpyridin-2-amine as an off-white solid in 23% yield. LCMS (m/z): 143 (MH$^+$); LC R$_t$=1.11 min.

Synthesis of 6-methyl-4-(4,4,5,5-tetramethyl-1,3,2-dioxaborolan-2-yl)pyridin-2-amine

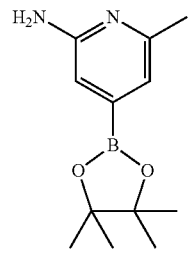

A solution 4-chloro-6-methylpyridin-2-amine (1.0 equiv.), potassium acetate (3.0 equiv.), bis(pinacolato)diboron (2.0 equiv.), tricyclohexylphosphine (0.075 equiv.) and Pd$_2$(dba)$_3$ (0.05 equiv.) in dioxane (0.12 M) was heated at 120° C. in a microwave for 2×15 minutes. The solution was filtered through a 1 μM HPLC filter, concentrated. DME was added and the resulting solid was filtered and rinsed with CH$_2$Cl$_2$. The combined filtrate was concentrated and pumped to yield 6-methyl-4-(4,4,5,5-tetramethyl-1,3,2-dioxaborolan-2-yl) pyridin-2-amine which was used directly. LC/MS=153.0 (M+H of corresponding HetB(OH)$_2$), LC=0.35 min.

Synthesis of 4-(6-chloro-1,7-naphthyridin-4-yl)-6-methylpyridin-2-amine

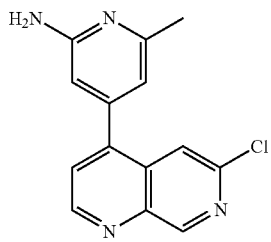 [SMILES: Cc1cc(-c2ccnc3cnc(Cl)cc23)cc(N)n1]

A solution of 6-chloro-1,7-naphthyridin-4-yl trifluoromethanesulfonate (1.0 equiv.), 6-methyl-4-(4,4,5,5-tetramethyl-1,3,2-dioxaborolan-2-yl)pyridin-2-amine (1.0 equiv.) and Pd(dppf)Cl$_2$—CH$_2$Cl$_2$ (0.1 equiv.) in 3:1 DME/2M Na$_2$CO$_3$ was heated in a microwave at 100° C. for 15 minutes. Upon cooling, the solution was partitioned between EtOAc and Na$_2$CO$_{3(sat.)}$ washed further with NaCl$_{(sat.)}$, dried over MgSO$_4$, concentrated and purified by silica gel chromatography (2-4% MeOH/CH$_2$Cl$_2$ w/0.1% DIEA eluant) to yield tert-butyl 4-(6-chloro-1,7-naphthyridin-4-yl)-6-methylpyridin-2-amine (17%). LC/MS=271.0 (M+H), LC=1.81 min.

Synthesis of 6-methyl-4-(6-(4,4,5,5-tetramethyl-1,3,2-dioxaborolan-2-yl)-1,7-naphthyridin-4-yl)pyridin-2-amine

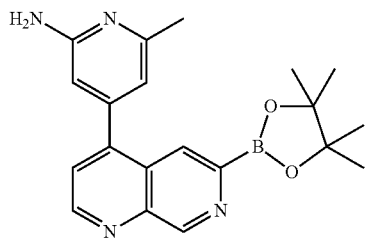 [SMILES: Cc1cc(-c2ccnc3cnc(B4OC(C)(C)C(C)(C)O4)cc23)cc(N)n1]

A solution tert-butyl 4-(6-chloro-1,7-naphthyridin-4-yl)-6-methylpyridin-2-ylcarbamate (1.0 equiv.), potassium acetate (3.0 equiv.), bis(pinacolato)diboron (2.0 equiv.), tricyclohexylphosphine (0.8 equiv.) and Pd$_2$(dba)$_3$ (0.2 equiv.) in dioxane (0.06 M) was heated at 135° C. in a microwave for 2×20 minutes. The solution was filtered through a 1 μM HPLC filter, concentrated and pumped to yield 6-methyl-4-(6-(4,4,5,5-tetramethyl-1,3,2-dioxaborolan-2-yl)-1,7-naphthyridin-4-yl)pyridin-2-amine which was used directly. LC/MS=281.1 (M+H of corresponding HetB(OH)$_2$), LC=1.09 min.

Synthesis of 2,6 dichloro-3N-(bisBocamino)pyridine

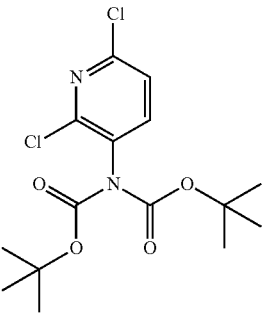 [SMILES: CC(C)(C)OC(=O)N(C(=O)OC(C)(C)C)c1ccc(Cl)nc1Cl]

A solution of 3-amino-2,6-dichloropyridine (1.0 equiv), di-tert-butyl dicarbonate (2.2 equiv.) and DMAP (0.2 equiv.) in CH$_2$Cl$_2$ (0.15 M) was stirred for 16 hours. Silica gel was added and upon concentration and purification by silica gel chromatography (10% EtOAc/hexanes eluant), 2,6 dichloro-3N-(bisBocamino)pyridine was obtained (83%). LC/MS=363.1 (M+H), LC=4.92 min.

Synthesis of 3-(5-amino-6-chloropyridin-2-yl)-4-fluoro-N-isopropylbenzamide

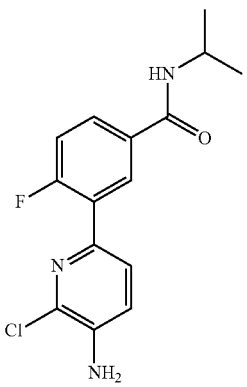 [SMILES: CC(C)NC(=O)c1ccc(F)c(-c2ccc(N)c(Cl)n2)c1]

A solution of 2,6 dichloro-3N-(bisBocamino)pyridine (1.0 equiv.), 2-fluoro-5-(isopropylcarbamoyl)phenylboronic acid (1.0 equiv.) and Pd(dppf)Cl$_2$—CH$_2$Cl$_2$ (0.05 equiv.) in 3:1 DME/2M Na$_2$CO$_3$ was heated at 90° C. for 15 hours. Upon cooling, the solution was partitioned between EtOAc and Na$_2$CO$_{3(sat.)}$ washed further with NaCl$_{(sat.)}$, dried over MgSO$_4$, concentrated and purified by silica gel chromatography (30-35% EtOAc/hexanes eluant) to yield bisBoc suzuki product. The Boc protected material was treated with 25% TFA/CH$_2$Cl$_2$ for 2 hours, the volatiles were removed in vacuo. The crude residue was diluted with EtOAc, washed with Na$_2$CO$_{3(sat.)}$ and NaCl$_{(sat.)}$, was dried over MgSO$_4$, was filtered and the volatiles were removed in vacuo yielding 3-(5-amino-6-chloropyridin-2-yl)-4-fluoro-N-isopropylbenzamide (60%). LC/MS=308.1 (M+H), LC=3.15 min.

Synthesis of 2-chloro-6-(2-fluorophenyl)pyridin-3-amine

A solution of 2,6 dichloro-3N-(bisBocamino)pyridine (1.0 equiv.), 2-fluorophenylboronic acid (1.0 equiv.) and Pd(dppf)Cl$_2$—CH$_2$Cl$_2$ (0.05 equiv.) in 3:1 DME/2M Na$_2$CO$_3$ was heated at 90° C. for 15 hours. Upon cooling, the solution was partitioned between EtOAc and Na$_2$CO$_{3(sat.)}$ washed further with NaCl$_{(sat.)}$, dried over MgSO$_4$, concentrated and purified by silica gel chromatography (10% EtOAc/hexanes eluant) to yield bisBoc suzuki product. The Boc protected material was treated with 25% TFA/CH$_2$Cl$_2$ for 2 hours, the volatiles were removed in vacuo. The crude residue was diluted with EtOAc, washed with Na$_2$CO$_{3(sat.)}$ and NaCl$_{(sat.)}$, was dried over MgSO$_4$, was filtered and the volatiles were removed in vacuo yielding 2-chloro-6-(2-fluorophenyl)pyridin-3-amine (57%). LC/MS=223.0 (M+H), LC=3.69 min.

Synthesis of 2-chloro-6-(2,6-difluorophenyl)pyridin-3-amine

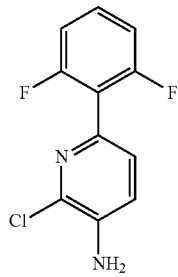 [SMILES: Nc1ccc(-c2c(F)cccc2F)nc1Cl]

A solution of 2,6 dichloro-3N-(bisBocamino)pyridine (1.0 equiv.), 2,6-difluorophenylboronic acid (1.0 equiv.) and Pd(dppf)Cl$_2$—CH$_2$Cl$_2$ (0.05 equiv.) in 3:1 DME/2M Na$_2$CO$_3$ was heated at 90° C. for 15 hours. Upon cooling, the solution was partitioned between EtOAc and Na$_2$CO$_{3(sat.)}$ washed further with NaCl$_{(sat.)}$, dried over MgSO$_4$, concentrated and purified by silica gel chromatography (5-10-20% EtOAc/hexanes eluant) to yield bisBoc suzuki product. The Boc protected material was treated with 25% TFA/CH$_2$Cl$_2$ for 2 hours, the volatiles were removed in vacuo. The crude residue was diluted with EtOAc, washed with Na$_2$CO$_{3(sat.)}$ and NaCl$_{(sat.)}$, was dried over MgSO$_4$, was filtered and the volatiles were removed in vacuo yielding 2-chloro-6-(2,6-difluorophenyl)pyridin-3-amine (15%). LC/MS=241.0 (M+H), LC=3.28 min.

Synthesis of 2,4-dichloropyrimidin-5-amine

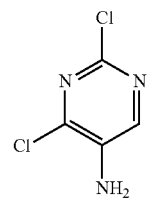

A heterogeneous solution of 2.4-dichloro-5-nitro-pyrimidine (1.0 eq.) and iron (6.0 eq) in acetic acid, at a concentration of 0.4 M, was stirred vigorously for 14 hours. The mixture was then passed through a celite pad, eluting with MeOH. Upon removal of the volatiles in vacuo, the residue was dissolved in EtOAc, washed with Na$_2$CO$_{3(sat.)}$, NaCl$_{(sat.)}$, was dried over MgSO$_4$, was filtered and the volatiles were removed in vacuo yielding 2,4-dichloropyrimidin-5-amine (80%). LCMS (m/z): 157.0 (MH$^+$); LC R$_t$=1.85 min.

Synthesis of 2,4 dichloro-5N-(bisBocamino)pyrimidine

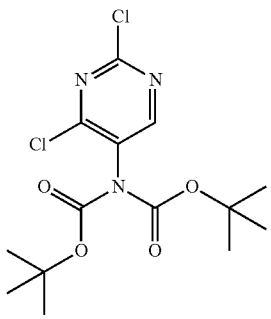 [SMILES: CC(C)(C)OC(=O)N(C(=O)OC(C)(C)C)c1cnc(Cl)nc1Cl]

A solution of 5-amino-2,4-dichloropyrimidine (1.0 equiv), di-tert-butyl dicarbonate (2.2 equiv.) and DMAP (0.2 equiv.) in CH$_2$Cl$_2$ (0.15 M) was stirred for 16 hours. Silica gel was added and upon concentration and purification by silica gel chromatography (10% EtOAc/hexanes eluant), 2,4 dichloro-5N-(bisBocamino)pyrimidine was obtained (48%). LC/MS=364.1 (M+H), LC=4.87 min.

Synthesis of 4-chloro-2-(2-fluorophenyl)pyrimidin-5-amine

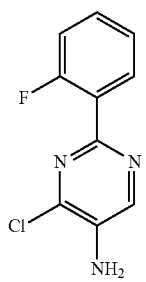 [SMILES: Nc1cnc(-c2ccccc2F)nc1Cl]

A solution of 2,4 dichloro-5N-(bisBocamino)pyrimidine (1.0 equiv.), 2-fluorophenylboronic acid (1.0 equiv.) and Pd(dppf)Cl$_2$—CH$_2$Cl$_2$ (0.05 equiv.) in 3:1 DME/2M Na$_2$CO$_3$ was heated at 90° C. for 15 hours. Upon cooling, the solution was partitioned between EtOAc and Na$_2$CO$_{3(sat.)}$ washed further with NaCl$_{(sat.)}$, dried over MgSO$_4$, concentrated and purified by silica gel chromatography (10% EtOAc/hexanes eluant) to yield bisBoc suzuki product. The Boc protected material was treated with 25% TFA/CH$_2$Cl$_2$ for 2 hours, the volatiles were removed in vacuo. The crude residue was diluted with EtOAc, washed with Na$_2$CO$_{3(sat.)}$ and NaCl$_{(sat.)}$, was dried over MgSO$_4$, was filtered and the volatiles were removed in vacuo yielding 4-chloro-2-(2-fluorophenyl)pyrimidin-5-amine (68%). LC/MS=224.0 (M+H), LC=2.71 min.

Synthesis of
2-chloro-6-(thiazol-2-yl)pyridin-3-amine

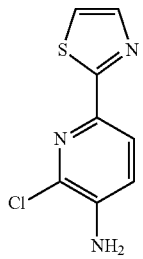

A solution of 2,6 dichloro-3N-(bisBocamino)pyridine (1.0 equiv.), (1.0 equiv.), 2-thiazolyl-zincbromide (3.5 equiv.), and Pd(dppf)Cl$_2$-DCM (0.10 equiv.) in THF was microwaved at 70° C. for 15 min. The reaction was filtered through celite, rinsed with EtOAc, concentrated to dryness under vacuo, and purification via silica gel chromatography to yield the Boc protected product (39%). The Boc protected material was treated with 25% TFA/CH$_2$Cl$_2$ for 2 hours, the volatiles were removed in vacuo. The crude residue was diluted with EtOAc, washed with Na$_2$CO$_{3(sat.)}$ and NaCl$_{(sat.)}$, was dried over MgSO$_4$, was filtered and the volatiles were removed in vacuo yielding 2-chloro-6-(thiazol-2-yl)pyridin-3-amine. LCMS (m/z): 212.1 (MH$^+$); LC R$_t$=2.70 min.

Method 1

Example 10

Synthesis of (S)-3-(5-amino-6-(4-(3-aminopiperidin-1-yl)-1,7-naphthyridin-6-yl)pyridin-2-yl)-4-fluoro-N-isopropylbenzamide

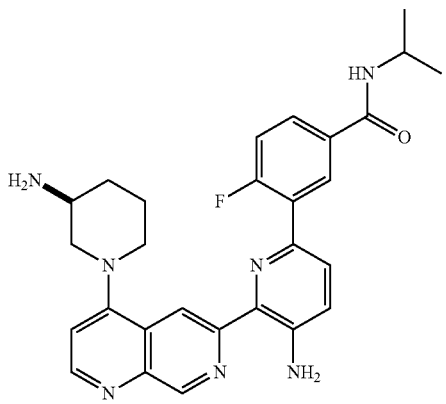 [SMILES: CC(C)NC(=O)c1ccc(F)c(-c2ccc(N)c(-c3cc4c(N5CCC[C@H](N)C5)ccnc4cn3)n2)c1]

A solution of (S)-tert-butyl 1-(6-(4,4,5,5-tetramethyl-1,3,2-dioxaborolan-2-yl)-1,7-naphthyridin-4-yl)piperidin-3-yl-carbamate (1.0 equiv.), 3-(5-amino-6-chloropyridin-2-yl)-4-fluoro-N-isopropylbenzamide ((1.0 equiv.) and Pd(dppf)Cl$_2$—CH$_2$Cl$_2$ (0.2 equiv.) in 3:1 DME/2M Na$_2$CO$_3$ was heated at 120° C. for 20 hours. Upon cooling, the solution was partitioned between EtOAc and Na$_2$CO$_{3(sat.)}$ washed further with NaCl$_{(sat.)}$, dried over MgSO$_4$, concentrated and purified by RP HPLC. Upon lyophilization, the Boc group was deprotected by treatment with 25% TFA/CH$_2$Cl$_2$, concentrated, purified by RP-HPLC and lyophilized to yield (S)-3-(5-amino-6-(4-(3-aminopiperidin-1-yl)-1,7-naphthyridin-6-yl)pyridin-2-yl)-4-fluoro-N-isopropylbenzamide (21%). LC/MS=500.3 (M+H), LC=2.36 min.

The compounds shown in the following Table 1 were made using the procedures of the foregoing Method 1:

TABLE 1

| Example # | Structure | Compound Name | MH+ | LC Rt |
|---|---|---|---|---|
| 1 | Chiral | (S)-2-(4-(3-aminopiperidin-1-yl)-3-fluoro-1,7-naphthyridin-6-yl)-6-(thiazol-2-yl)pyridin-3-amine | 422.1 | 2.35 |

TABLE 1-continued

| Example # | Structure | Compound Name | MH+ | LC Rt |
|---|---|---|---|---|
| 2 | Chiral | (S)-3-(5-amino-6-(4-(3-aminopiperidin-1-yl)-3-fluoro-1,7-naphthyridin-6-yl)-pyridin-2-yl)-4-fluoro-N-isopropylbenzamide | 518.2 | 2.82 |
| 3 | 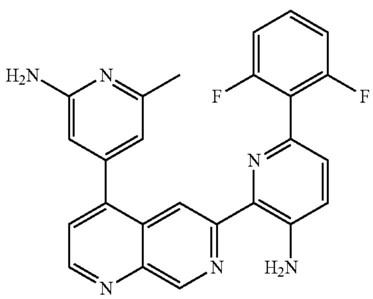 [SMILES: Cc1cc(-c2ccnc3cnc(-c4nc(-c5c(F)cccc5F)ccc4N)cc23)cc(N)n1] | 4-(6-(3-amino-6-(2,6-difluorophenyl)pyridin-2-yl)-1,7-naphthyridin-4-yl)-6-methylpyridin-2-amine | 441.1 | 2.60 |
| 4 | 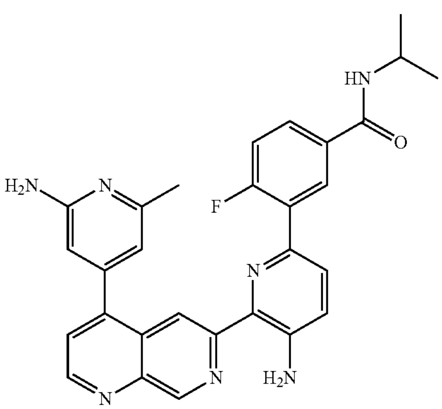 [SMILES: Cc1cc(-c2ccnc3cnc(-c4nc(-c5cc(C(=O)NC(C)C)ccc5F)ccc4N)cc23)cc(N)n1] | 3-(5-amino-6-(4-(2-amino-6-methyl-pyridin-4-yl)-1,7-naphthyridin-6-yl)-pyridin-2-yl)-4-fluoro-N-isopropylbenzamide | 508.2 | 2.57 |
| 5 | Chiral | (S)-2-(4-(3-amino-piperidin-1-yl)-1,7-naphthyridin-6-yl)-6-(thiazol-2-yl)pyridin-3-amine | 404.1 | 1.81 |

TABLE 1-continued

| Example # | Structure | Compound Name | MH+ | LC Rt |
|---|---|---|---|---|
| 6 | Chiral | (S)-4-(4-(3-amino-piperidin-1-yl)-1,7-naphthyridin-6-yl)-2-(2-fluorophenyl)-pyrimidin-5-amine | 416.2 | 1.87 |
| 7 | Chiral | (R)-2-(4-(3-amino-piperidin-1-yl)-1,7-naphthyridin-6-yl)-6-(2,6-difluorophenyl)-pyridin-3-amine | 433.2 | 2.17 |
| 8 | Chiral | (R)-3-(5-amino-6-(4-(3-aminopiperidin-1-yl)-1,7-naphthyridin-6-yl)pyridin-2-yl)-4-fluoro-N-isopropyl-benzamide | 500.3 | 2.24 |
| 9 | Chiral | (S)-2-(4-(3-amino-piperidin-1-yl)-1,7-naphthyridin-6-yl)-6-(2,6-difluorophenyl)-pyridin-3-amine | 433.2 | 2.17 |

TABLE 1-continued

| Example # | Structure | Compound Name | MH+ | LC Rt |
|---|---|---|---|---|
| 10 | 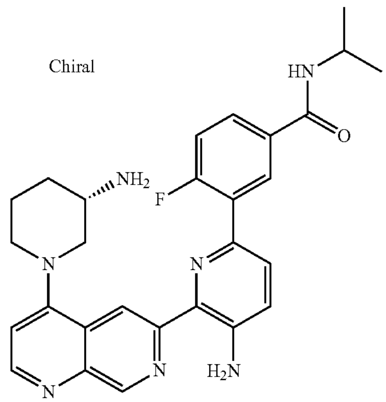 [SMILES: CC(C)NC(=O)c1ccc(F)c(-c2ccc(N)c(-c3cc4c(N5CCC[C@H](N)C5)ccnc4cn3)n2)c1] | (S)-3-(5-amino-6-(4-(3-aminopiperidin-1-yl)-1,7-naphthyridin-6-yl)pyridin-2-yl)-4-fluoro-N-isopropyl-benzamide | 500.3 | 2.24 |
| 11 | 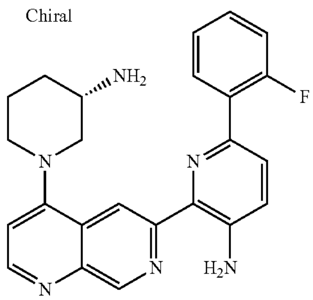 [SMILES: Nc1ccc(-c2ccccc2F)nc1-c1cc2c(N3CCC[C@H](N)C3)ccnc2cn1] | (S)-2-(4-(3-amino piperidin-1-yl)-1,7-naphthyridin-6-yl)-6-(2-fluorophenyl)-pyridin-3-amine | 415.2 | 2.16 |

Synthesis of (S)-tert-butyl 1-(6-(6-chloro-3-nitropyridin-2-yl)-1,7-naphthyridin-4-yl)piperidin-3-ylcarbamate

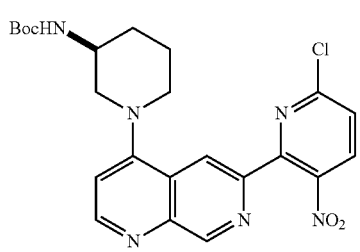 [SMILES: CC(C)(C)OC(=O)N[C@H]1CCCN(c2ccnc3cnc(-c4nc(Cl)ccc4[N+](=O)[O-])cc23)C1]

A solution of (S)-tert-butyl 1-(6-(4,4,5,5-tetramethyl-1,3,2-dioxaborolan-2-yl)-1,7-naphthyridin-4-yl)piperidin-3-ylcarbamate (1.0 equiv.), 2.6 dichloro 3-nitropyridine (1.0 equiv.) and Pd(dppf)Cl$_2$—CH$_2$Cl$_2$ (0.15 equiv.) in 3:1 DME/2M Na$_2$CO$_3$ was heated in a microwave at 100° C. for 20 minutes. Upon cooling, the solution was partitioned between EtOAc and Na$_2$CO$_{3(sat.)}$ washed further with NaCl$_{(sat.)}$, dried over MgSO$_4$, concentrated and purified by silica gel chromatography (75% EtOAc/hexanes eluant) to yield (S)-tert-butyl 1-(6-(6-chloro-3-nitropyridin-2-yl)-1,7-naphthyridin-4-yl)piperidin-3-ylcarbamate (20%). LC/MS=485.1 (M+H), LC=3.17 min.

Synthesis of (S)-tert-butyl 1-(6-(3-amino-6-chloropyridin-2-yl)-1,7-naphthyridin-4-yl)piperidin-3-yl-carbamate

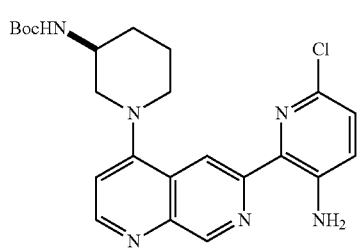 [SMILES: CC(C)(C)OC(=O)N[C@H]1CCCN(c2ccnc3cnc(-c4nc(Cl)ccc4N)cc23)C1]

A heterogeneous solution of (S)-tert-butyl 1-(6-(6-chloro-3-nitropyridin-2-yl)-1,7-naphthyridin-4-yl)piperidin-3-ylcarbamate (1.0 eq.) and iron (6.0 eq) in acetic acid, at a concentration of 0.4 M, was stirred vigorously for 14 hours. The mixture was then passed through a celite pad, eluting with MeOH. Upon removal of the volatiles in vacuo, the residue was dissolved in EtOAc, washed with Na$_2$CO$_{3(sat.)}$, NaCl$_{(sat.)}$, was dried over MgSO$_4$, was filtered and the volatiles were removed in vacuo yielding (S)-tert-butyl 1-(6-(3-amino-6-chloropyridin-2-yl)-1,7-naphthyridin-4-yl)piperidin-3-ylcarbamate (77%). LCMS (m/z): 455.2 (MH$^+$); LC R$_t$=3.10 min.

Method 2

Example 19

Synthesis of (S)-2-(4-(3-aminopiperidin-1-yl)-1,7-naphthyridin-6-yl)-6-(4-fluorophenyl)pyridin-3-amine

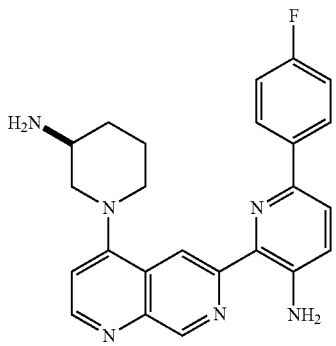 [SMILES: Nc1ccc(-c2ccc(F)cc2)nc1-c1cc2c(N3CCC[C@H](N)C3)ccnc2cn1]

A solution of (S)-tert-butyl 1-(6-(3-amino-6-chloropyridin-2-yl)-1,7-naphthyridin-4-yl)piperidin-3-ylcarbamate (1.0 equiv.), 4-fluorophenylboronic acid (3.0 equiv.) and Pd(dppf)Cl$_2$—CH$_2$Cl$_2$ (0.15 equiv.) in 3:1 DME/2M Na$_2$CO$_3$ was heated in a microwave at 120° C. for 20 minutes. Upon cooling, the solution was partitioned between EtOAc and Na$_2$CO$_{3(sat.)}$ washed further with NaCl$_{(sat.)}$, dried over MgSO$_4$, concentrated and purified by RP HPLC. Upon lyophilization, the Boc group was deprotected by treatment with 25% TFA/CH$_2$Cl$_2$, concentrated, purified by RP-HPLC and lyophilized to yield (S)-2-(4-(3-aminopiperidin-1-yl)-1,7-naphthyridin-6-yl)-6-(4-fluorophenyl)pyridin-3-amine (61%). LC/MS=415.2 (M+H), LC=2.32 min.

The compounds shown in the following Table 2 were made using the procedures of the foregoing Method 2:

TABLE 2

| Example # | Structure | Compound Name | MH+ | LC Rt |
|---|---|---|---|---|
| 12 | Chiral | (S)-3-(5-amino-6-(4-(3-aminopiperidin-1-yl)-1,7-naphthyridin-6-yl)pyridin-2-yl)-4-fluoro-N-phenylbenzamide | 534.3 | 2.50 |
| 13 | Chiral | (S)-2-(4-(3-aminopiperidin-1-yl)-1,7-naphthyridin-6-yl)-6-(thiophen-2-yl)pyridin-3-amine | 403.2 | 2.09 |
| 14 | Chiral | (S)-6-(4-(3-aminopiperidin-1-yl)-1,7-naphthyridin-6-yl)-6'-methoxy-2,2'-bipyridin-5-amine | 428.2 | 2.00 |

TABLE 2-continued

| Example # | Structure | Compound Name | MH+ | LC Rt |
|---|---|---|---|---|
| 15 | Chiral 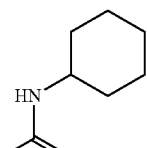 | (S)-3-(5-amino-6-(4-(3-aminopiperidin-1-yl)-1,7-naphthyridin-6-yl)pyridin-2-yl)-N-cyclohexyl-4-fluorobenzamide | 540.3 | 2.70 |
| 16 | Chiral 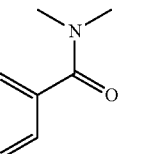 | (S)-3-(5-amino-6-(4-(3-aminopiperidin-1-yl)-1,7-naphthyridin-6-yl)pyridin-2-yl)-4-fluoro-N,N-dimethylbenzamide | 486.3 | 2.18 |
| 17 | Chiral 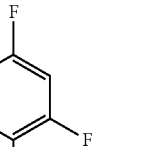 | (S)-2-(4-(3-aminopiperidin-1-yl)-1,7-naphthyridin-6-yl)-6-(2,4-difluorophenyl)pyridin-3-amine | 433.2 | 2.43 |
| 18 | Chiral 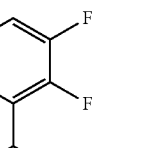 | (S)-2-(4-(3-aminopiperidin-1-yl)-1,7-naphthyridin-6-yl)-6-(2,3-difluorophenyl)pyridin-3-amine | 433.2 | 2.46 |

TABLE 2-continued

| Example # | Structure | Compound Name | MH+ | LC Rt |
|---|---|---|---|---|
| 19 | Chiral | (S)-2-(4-(3-aminopiperidin-1-yl)-1,7-naphthyridin-6-yl)-6-(4-fluorophenyl)pyridin-3-amine | 415.2 | 2.32 |
| 20 | CHIRAL | (S)-2-(4-(3-aminopiperidin-1-yl)-1,7-naphthyridin-6-yl)-6-phenylpyridin-3-amine | 397.2 | 2.22 |
| 21 | Chiral | (S)-3-(5-amino-6-(4-(3-aminopiperidin-1-yl)-1,7-naphthyridin-6-yl)pyridin-2-yl)benzenesulfonamide | 476.2 | 1.92 |
| 22 | Chiral | (S)-2-(4-(3-aminopiperidin-1-yl)-1,7-naphthyridin-6-yl)-6-(3-(methylsulfonyl)phenyl)pyridin-3-amine | 475.2 | 2.07 |

TABLE 2-continued

| Example # | Structure | Compound Name | MH+ | LC Rt |
|---|---|---|---|---|
| 23 | Chiral | (S)-4-(5-amino-6-(4-(3-aminopiperidin-1-yl)-1,7-naphthyridin-6-yl)pyridin-2-yl)benzenesulfonamide | 476.2 | 1.87 |
| 24 | Chiral | (S)-2-(4-(3-aminopiperidin-1-yl)-1,7-naphthyridin-6-yl)-6-(4-(methylsulfonyl)phenyl)pyridin-3-amine | 475.2 | 2.05 |

Synthesis of (S)-tert-butyl 1-(6-bromoquinolin-4-yl)piperidin-3-ylcarbamate

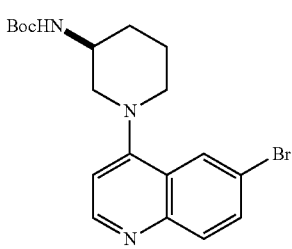 [SMILES: CC(C)(C)OC(=O)N[C@H]1CCCN(c2ccnc3ccc(Br)cc23)C1]

A solution of 6-bromo-4-chloroquinoline (1.0 equiv.), (S)-tert-butyl piperidin-3-ylcarbamate (1.0 equiv.) and DIEA (1.5 equiv.) in NMP (0.1 M) was heated at 140° C. for 48 hours. Upon cooling the solution was poured onto ice and upon melting the solid was filtered, rinsed with $H_2O$ and pumped on to yield (S)-tert-butyl 1-(6-bromoquinolin-4-yl)piperidin-3-ylcarbamate. LC/MS=406.0/408.0 (M+H), LC=2.85 min.

Synthesis of (S)-tert-butyl 1-(6-(4,4,5,5-tetramethyl-1,3,2-dioxaborolan-2-yl)quinolin-4-yl)piperidin-3-ylcarbamate

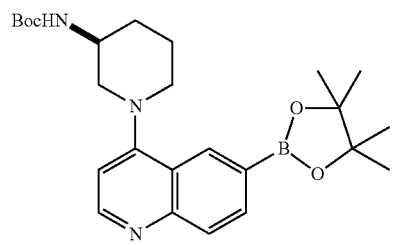 [SMILES: CC(C)(C)OC(=O)N[C@H]1CCCN(c2ccnc3ccc(B4OC(C)(C)C(C)(C)O4)cc23)C1]

A solution (S)-tert-butyl 1-(6-bromoquinolin-4-yl)piperidin-3-ylcarbamate (1.0 equiv.), potassium acetate (3.0 equiv.), bis(pinacolato)diboron (2.0 equiv.), tricyclohexylphosphine (0.2 equiv.) and $Pd_2(dba)_3$ (0.05 equiv.) in dioxane (0.05 M) was heated at 135° C. in a microwave for 20 minutes. The solution was filtered through a 1 μM HPLC filter, concentrated and pumped to yield (S)-tert-butyl 1-(6-(4,4,5,5-tetramethyl-1,3,2-dioxaborolan-2-yl)quinolin-4-yl)piperidin-3-ylcarbamate which was used directly. LC/MS=372.1 (M+H of corresponding HetB(OH)$_2$), LC=2.26 min.

Synthesis of 6-(thiazol-2-yl)pyridin-2-yl trifluoromethanesulfonate

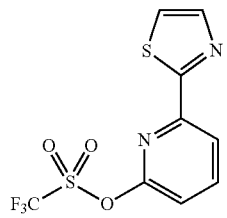 [SMILES: O=S(=O)(Oc1cccc(-c2nccs2)n1)C(F)(F)F]

A solution of 2-bromo-6-methoxypyridine (1.0 equiv.), 0.5 M 2-thiazole-zincbromide in THF (2 equiv.) and Pd(dppf)Cl₂-DCM (0.2 equiv.) in a THF (0.1 M) was heated at 100° C. for 20 min in a microwave. Upon cooling, the solution was partitioned between EtOAc and Na₂CO₃(sat.) washed further with NaCl(sat.), dried over MgSO₄, concentrated and purified by silica gel chromatography (20% EtOAc/hexanes eluant) to yield 2-(6-methoxypyridin-2-yl)thiazole (73%). The material was treated with dioxane/H₂O/HCl(conc.) in a 3:1:0.25 ratio at 100° C. for 72 hours. Upon removal of the volatiles in vacuo, a solution of the crude hydroxylpyridine (1.0 equiv.), diisopropylethylamine (2.0 equiv.), and 1,1,1-trifluoro-N-phenyl-N-(trifluoromethylsulfonyl)methanesulfonamide (1.5 equiv.) in CH₂Cl₂ was stirred for 16 hours. The solution was partitioned between EtOAc and Na₂CO₃(sat.). Upon separation, the organic layer was washed further with Na₂CO₃(sat.) and NaCl(sat.), dried over MgSO₄, concentrated and purified by silica gel chromatography to yield 6-(thiazol-2-yl)pyridin-2-yl trifluoromethanesulfonate.

Synthesis of 6-(2,6-difluorophenyl)pyridin-2-yl trifluoromethanesulfonate

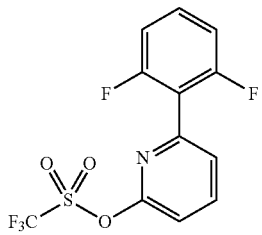 [SMILES: O=S(=O)(Oc1cccc(-c2c(F)cccc2F)n1)C(F)(F)F]

A solution of 2-bromo-6-methoxypyridine (1.0 equiv.), 2,6-difluorophenylboronic acid (2 equiv.) and Pd(dppf)Cl₂-DCM (0.05 equiv.) in 3:1 DME/2M Na₂CO₃ was heated at 110° C. for 48 hours. Upon cooling, the solution was partitioned between EtOAc and Na₂CO₃(sat.) washed further with NaCl(sat.), dried over MgSO₄, concentrated and purified by silica gel chromatography (10-20% EtOAc/hexanes eluant) to yield the Suzuki product. The material was treated with dioxane/H₂O/HCl(conc.) in a 3:1:0.25 ratio at 100° C. for 72 hours. Upon removal of the volatiles in vacuo, a solution of the crude hydroxylpyridine (1.0 equiv.), diisopropylethylamine (2.0 equiv.), and 1,1,1-trifluoro-N-phenyl-N-(trifluoromethylsulfonyl)methanesulfonamide (1.5 equiv.) in CH₂Cl₂ was stirred for 16 hours. The solution was partitioned between EtOAc and Na₂CO₃(sat.). Upon separation, the organic layer was washed further with Na₂CO₃(sat.) and NaCl(sat.), dried over MgSO₄, concentrated and purified by silica gel chromatography to yield 6-(2,6-difluorophenyl)pyridin-2-yl trifluoromethanesulfonate.

Method 3

Example 27

Synthesis of (S)-1-(6-(6-(thiazol-2-yl)pyridin-2-yl)quinolin-4-yl)piperidin-3-amine

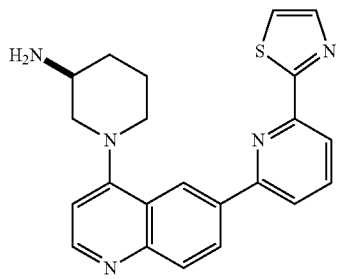 [SMILES: N[C@H]1CCCN(c2ccnc3ccc(-c4cccc(-c5nccs5)n4)cc23)C1]

A solution of (S)-tert-butyl 1-(6-(4,4,5,5-tetramethyl-1,3,2-dioxaborolan-2-yl)quinolin-4-yl)piperidin-3-ylcarbamate (1.0 equiv.), 6-(thiazol-2-yl)pyridin-2-yl trifluoromethanesulfonate (1.5 equiv.) and Pd(dppf)Cl₂—CH₂Cl₂ (0.15 equiv.) in 3:1 DME/2M Na₂CO₃ was heated in a microwave at 100° C. for 20 minutes. Upon cooling, the solution was partitioned between EtOAc and Na₂CO₃(sat.) washed further with NaCl(sat.), dried over MgSO₄, concentrated and purified by RP HPLC. Upon lyophilization, the Boc group was deprotected by treatment with 25% TFA/CH₂Cl₂, concentrated, purified by RP-HPLC and lyophilized to yield (S)-1-(6-(6-(thiazol-2-yl)pyridin-2-yl)quinolin-4-yl)piperidin-3-amine (40%). LC/MS=388.1 (M+H), LC=2.02 min.

The compounds shown in the following Table 3 were made using the procedures of the foregoing Method 3:

TABLE 3

| Example # | Structure | Compound Name | MH+ | LC Rt |
|---|---|---|---|---|
| 25 | Chiral | (S)-1-(6-(6-(thiazol-2-yl)pyridin-2-yl)-1,7-naphthyridin-4-yl)piperidin-3-amine | 389.1 | 1.92 |

TABLE 3-continued

| Example # | Structure | Compound Name | MH+ | LC Rt |
|---|---|---|---|---|
| 26 | 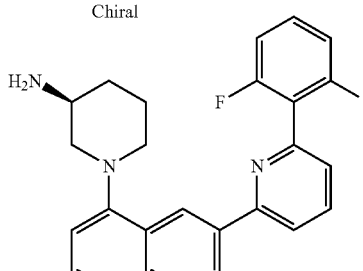 | (S)-1-(6-(6-(2,6-difluorophenyl)pyridin-2-yl)quinolin-4-yl)piperidin-3-amine | 417.1 | 2.32 |
| 27 | 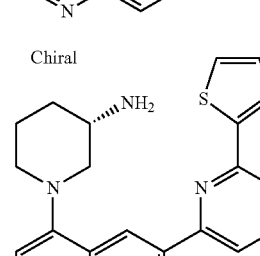 | (S)-1-(6-(6-(thiazol-2-yl)pyridin-2-yl)quinolin-4-yl)piperidin-3-amine | 388.1 | 2.02 |

Synthesis of 4-(benzyloxy)-2-chloropyrimidine

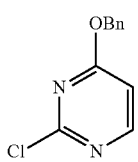

To a cooled (1-2° C.) suspension of sodium hydride (60% in mineral oil) (1.5 equiv) in 250 ml THF, benzyl alcohol (1.0 equiv.) was added dropwise and the mixture stirred 30 min under $N_2$. This suspension was then added in small portions (via syringe, over 1 hr) to a solution of 2,4-dichloropyrimidine (1.5 equiv.) in THF also at 1-2° C. (internal thermometer). The resulting mixture (0.06 M) was stirred at temp <2° C. for 2.5 hrs, then quenched with $NH_4Cl_{(sat.)}$ and extracted with EtOAc. Upon separation, the organic layer was washed with $NaCl_{(sat.)}$, dried over $Na_2SO_4$, concentrated and purified by silica gel chromatography (hexanes/DCM eluant) to yield 4-(benzyloxy)-2-chloropyrimidine (24%). LC/MS=221.0 (M+H), LC=3.93 min.

Synthesis of (S)-tert-butyl 1-(6-(4-(benzyloxy)pyrimidin-2-yl)quinolin-4-yl)piperidin-3-ylcarbamate

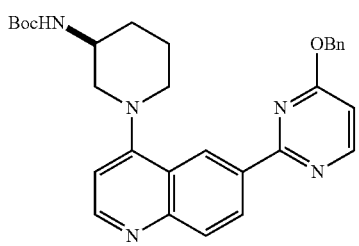 [SMILES: CC(C)(C)OC(=O)N[C@H]1CCCN(c2ccnc3ccc(-c4nccc(OCc5ccccc5)n4)cc23)C1]

To a mixture of (S)-tert-butyl 1-(6-(4,4,5,5-tetramethyl-1,3,2-dioxaborolan-2-yl)quinolin-4-yl)piperidin-3-ylcarbamate (1.0 equiv.), 4-(benzyloxy)-2-chloropyrimidine (2.0 equiv.) and Pd(dppf)Cl$_2$-DCM (0.15 equiv) in a 20 ml microwave vial, DME and 2M Na$_2$CO$_3$ were added (1.0 M). The vial was submitted to 125° C. for 20 min in microwave. The resulting mixture was partitioned between EtOAc and H$_2$O. Upon separation, the organic layer was washed with NaCl$_{(sat.)}$, dried over Na$_2$SO$_4$, concentrated and purified by reverse-phase HPLC to yield (S)-tert-butyl 1-(6-(4-(benzyloxy)pyrimidin-2-yl)quinolin-4-yl)piperidin-3-ylcarbamate (88%). LC/MS=512.1 (M+H), LC=3.40 min.

Synthesis of (S)-tert-butyl 1-(6-(6-oxo-1,6-dihydropyrimidin-2-yl)quinolin-4-yl)piperidin-3-ylcarbamate

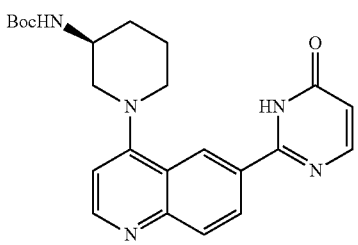 [SMILES: CC(C)(C)OC(=O)N[C@H]1CCCN(c2ccnc3ccc(-c4nccc(=O)[nH]4)cc23)C1]

To a solution of (S)-tert-butyl 1-(6-(4-(benzyloxy)pyrimidin-2-yl)quinolin-4-yl)piperidin-3-ylcarbamate (1.0 equiv.) in 4:1 EtOH/EtOAc (0.6 M), was added 10% palladium on carbon (0.2 eq.). The resulting heterogeneous solution was stirred for 12 hours under an atmosphere of hydrogen. The mixture was then filtered through a pad of celite eluting with EtOAc. The volatiles were removed in vacuo yielding (S)-tert-butyl 1-(6-(6-oxo-1,6-dihydropyrimidin-2-yl)quinolin-4-yl)piperidin-3-ylcarbamate (87%). LCMS (m/z): 422.1 (MH$^+$); LC R$_t$=2.14 min.

Synthesis of (S)-2-(4-(3-(tert-butoxycarbonylamino)piperidin-1-yl)quinolin-6-yl)pyrimidin-4-yl trifluoromethanesulfonate

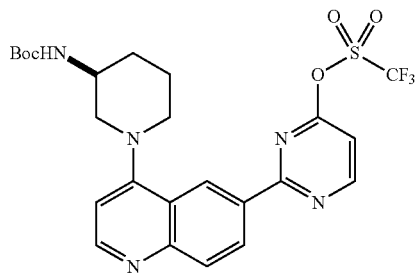 [SMILES: CC(C)(C)OC(=O)N[C@H]1CCCN(c2ccnc3ccc(-c4nccc(OS(=O)(=O)C(F)(F)F)n4)cc23)C1]

A solution of (S)-tert-butyl 1-(6-(6-oxo-1,6-dihydropyrimidin-2-yl)quinolin-4-yl)piperidin-3-ylcarbamate (1.0 equiv.), diisopropylethylamine (2.0 equiv.), and 1,1,1-trifluoro-N-phenyl-N-(trifluoromethylsulfonyl)methanesulfonamide (1.5 equiv.) in $CH_2Cl_2$ (0.13 M) was submitted to 105° C. for 3×20 min in microwave, concentrated and purified by silica gel chromatography (80% EtOAc/hexanes eluant) to yield (S)-2-(4-(3-(tert-butoxycarbonylamino)piperidin-1-yl)quinolin-6-yl)pyrimidin-4-yl trifluoromethanesulfonate (50%). LC/MS=554.1 (M+H), LC=3.62 min.

Example 28

Synthesis of (S)-1-(6-(4-(thiazol-2-yl)pyrimidin-2-yl)quinolin-4-yl)piperidin-3-amine

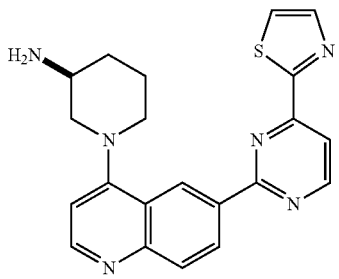 [SMILES: N[C@H]1CCCN(c2ccnc3ccc(-c4nccc(-c5nccs5)n4)cc23)C1]

0.5M 2-thiazole-zincbromide solution in THF (10 equiv.) was added to (S)-2-(4-(3-(tert-butoxycarbonylamino)piperidin-1-yl)quinolin-6-yl)pyrimidin-4-yl trifluoromethanesulfonate (1.0 equiv.) (0.045 M) and Pd(dppf)$Cl_2$-DCM (0.2 equiv.) in a microwave vial and the mixture submitted to 100° C. for 10 min in microwave, filtered through 1 μm PTFE HPLC filter, eluting with EtOAc and concentrated. The resulting (S)-tert-butyl 1-(6-(4-(thiazol-2-yl)pyrimidin-2-yl)quinolin-4-yl)piperidin-3-ylcarbamate was dissolved in 25% TFA/DCM (0.011 M) and allowed to sit for 2 hrs, concentrated and purified by reverse-phase HPLC to yield (S)-1-(6-(4-(thiazol-2-yl)pyrimidin-2-yl)quinolin-4-yl)piperidin-3-amine (100%). LC/MS=389.2 (M+H), LC=1.97 min.

Method 4

Example 29

Synthesis of (S)-1-(6-(4-(2,6-difluorophenyl)pyrimidin-2-yl)quinolin-4-yl)piperidin-3-amine

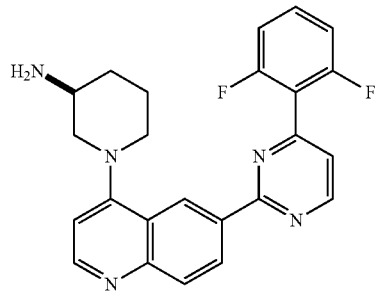 [SMILES: N[C@H]1CCCN(c2ccnc3ccc(-c4nccc(-c5c(F)cccc5F)n4)cc23)C1]

To a solution of (S)-2-(4-(3-(tert-butoxycarbonylamino)piperidin-1-yl)quinolin-6-yl)pyrimidin-4-yl trifluoromethanesulfonate (1.0 equiv.) in DME, 2,6-difluoroboronic acid (3.0 equiv.), Pd(dppf)$Cl_2$-DCM (0.2 equiv) and 2M $Na_2CO_3$ (0.03 M) were added in a microwave vial, which was then submitted to 120° C. for 15 min in the microwave. The resulting organic layer was isolated, concentrated and dissolved in 25% TFA/DCM (0.023 M). After about 1 hr of sitting, the reaction mixture was concentrated and purified by reverse-phase HPLC to yield (S)-1-(6-(4-(2,6-difluorophenyl)pyrimidin-2-yl)quinolin-4-yl)piperidin-3-amine (100%). LC/MS=418.2 (M+H), LC=2.21 min.

The compounds shown in the following Table 4 were made using the procedures of the foregoing Method 4:

TABLE 4

| Example # | Structure | Compound Name | MH+ | LC Rt |
|---|---|---|---|---|
| 29 | Chiral  $H_2N$  F  F | (S)-1-(6-(4-(2-fluorophenyl)pyrimidin-2-yl)quinolin-4-yl)piperidin-3-amine | 418.2 | 2.21 |

TABLE 4-continued

| Example # | Structure | Compound Name | MH+ | LC Rt |
|---|---|---|---|---|
| 30 | 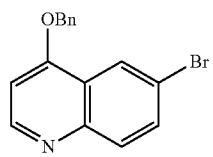 [SMILES: Brc1ccc2nccc(OCc3ccccc3)c2c1] | (S)-1-(6-(4-(2,6-difluorophenyl)pyrimidin-2-yl)quinolin-4-yl)piperidin-3-amine | 400.2 | 2.30 |

Synthesis of 4-(benzyloxy)-6-bromoquinoline

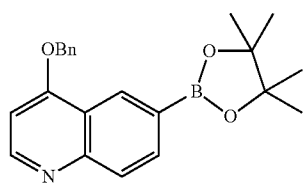 [SMILES: CC1(C)OB(c2ccc3nccc(OCc4ccccc4)c3c2)OC1(C)C]

To a solution of 60% NaH in mineral oil (1.75 equiv.) in DMF (0.5 M) was added benzyl alcohol (2.5 equiv.) dropwise. After stirring for 30 minutes, 6-bromo-4-chloroquinoline (1.0 equiv.) was added and the solution was heated in a microwave at 100° C. for 30 minutes. Upon cooling, the solution was partitioned between EtOAc and H$_2$O. Upon separation, the organic layer was washed further with H$_2$O (3×) and NaCl$_{(sat.)}$, dried over MgSO$_4$, concentrated and triturated with hexanes to yield 4-(benzyloxy)-6-bromoquinoline (73%). LC/MS=314.0/315.9 (M+H), LC=2.89 min.

Synthesis of 4-(benzyloxy)-6-(4,4,5,5-tetramethyl-1,3,2-dioxaborolan-2-yl)quinoline

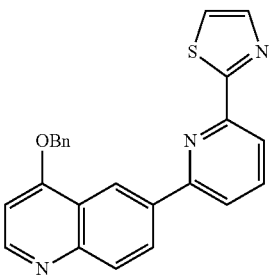 [SMILES: c1ccc(COc2ccnc3ccc(-c4cccc(-c5nccs5)n4)cc23)cc1]

A solution 4-(benzyloxy)-6-bromoquinoline (1.0 equiv.), potassium acetate (3.0 equiv.), bis(pinacolato)diboron (2.0 equiv.), tricyclohexylphosphine (0.2 equiv.) and Pd$_2$(dba)$_3$ (0.05 equiv.) in dioxane (0.05 M) was heated at 135° C. in a microwave for 20 minutes. The solution was filtered through a 1 μM HPLC filter, concentrated and pumped to yield 4-(benzyloxy)-6-(4,4,5,5-tetramethyl-1,3,2-dioxaborolan-2-yl) quinoline, which was used directly. LC/MS=362.0/279.9 (M+H of product & corresponding HetB(OH)$_2$), LC=3.39 min and 2.11 min for corresponding Het(B(OH)$_2$.

Synthesis of 2-(6-(4-(benzyloxy)quinolin-6-yl)pyridin-2-yl)thiazole

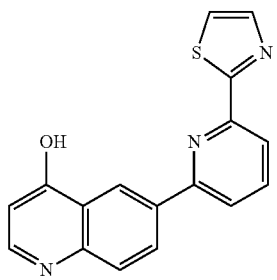 [SMILES: Oc1ccnc2ccc(-c3cccc(-c4nccs4)n3)cc12]

A solution of 4-(benzyloxy)-6-(4,4,5,5-tetramethyl-1,3,2-dioxaborolan-2-yl)quinoline (1.0 equiv.), 6-(thiazol-2-yl)pyridin-2-yl trifluoromethanesulfonate (1.0 equiv.) and Pd(dppf)Cl$_2$—CH$_2$Cl$_2$ (0.1 equiv.) in 3:1 DME/2M Na$_2$CO$_3$ was heated in a microwave at 120° C. for 20 minutes. Upon cooling, the solution was partitioned between EtOAc and H$_2$O. Upon separation, the organic layer was washed with NaCl$_{(sat.)}$, dried over MgSO$_4$, concentrated and purified by silica gel chromatography (EtOAc eluant) to yield 2-(6-(4-(benzyloxy)quinolin-6-yl)pyridin-2-yl)thiazole (39%). LC/MS=396.0 (M+H), LC=3.34 min.

Synthesis of 6-(6-(thiazol-2-yl)pyridin-2-yl)quinolin-4-ol

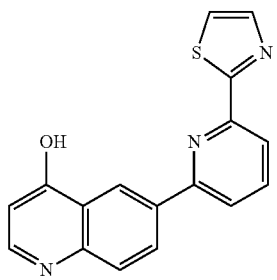 [SMILES: Oc1ccnc2ccc(-c3cccc(-c4nccs4)n3)cc12]

To a solution of 2-(6-(4-(benzyloxy)quinolin-6-yl)pyridin-2-yl)thiazole (1.0 equiv.) in 1:1 EtOH/EtOAc, at a concentration of 0.1 M, was added 10% palladium on carbon (0.1 eq.). The resultant heterogeneous solution was put under an atmosphere of hydrogen and was stirred for 72 hours. At this time the mixture was filtered through a pad of celite eluting with EtOAc. The volatiles were removed in vacuo yielding 6-(6-(thiazol-2-yl)pyridin-2-yl)quinolin-4-ol (88%). LCMS (m/z): 305.9 (MH$^+$); LC R$_t$=2.57 min.

Synthesis of 6-(6-(thiazol-2-yl)pyridin-2-yl)quinolin-4-yl trifluoromethanesulfonate

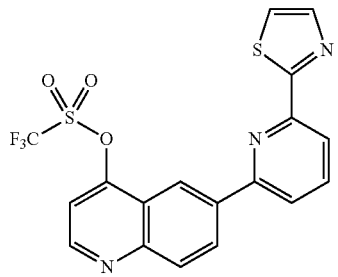 [SMILES: O=S(=O)(Oc1ccnc2ccc(-c3cccc(-c4nccs4)n3)cc12)C(F)(F)F]

A solution of 6-(6-(thiazol-2-yl)pyridin-2-yl)quinolin-4-ol (1.0 equiv.), diisopropylethylamine (2.0 equiv.), and 1,1,1-trifluoro-N-phenyl-N-(trifluoromethylsulfonyl)methanesulfonamide (1.5 equiv.) in NMP (0.23 M) was stirred for 72 hours. The solution was partitioned between EtOAc and Na$_2$CO$_{3(sat.)}$. Upon separation, the organic layer was washed further with Na$_2$CO$_{3(sat.)}$ and NaCl$_{(sat.)}$, dried over MgSO$_4$, concentrated and purified by silica gel chromatography (50% EtOAc/hexanes eluant) to yield 6-(6-(thiazol-2-yl)pyridin-2-yl)quinolin-4-yl trifluoromethanesulfonate (47%). LC/MS=437.9 (M+H), LC=4.91 min.

Synthesis of 4-(benzyloxy)-6-(6-bromopyridin-2-yl)quinoline

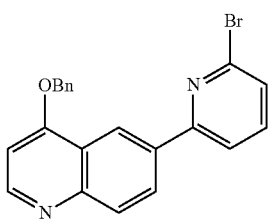 [SMILES: Brc1cccc(-c2ccc3nccc(OCc4ccccc4)c3c2)n1]

A solution of 4-(benzyloxy)-6-(4,4,5,5-tetramethyl-1,3,2-dioxaborolan-2-yl)quinoline (1.0 equiv.), 2,6 dibromopyridine (1.0 equiv.) and Pd(dppf)Cl$_2$—CH$_2$Cl$_2$ (0.1 equiv.) in 3:1 DME/2M Na$_2$CO$_3$ was heated in a microwave at 100° C. for 20 minutes. Upon cooling, the solution was partitioned between EtOAc and H$_2$O. Upon separation, the organic layer was washed with NaCl$_{(sat.)}$, dried over MgSO$_4$, concentrated and purified by silica gel chromatography (70-90 EtOAc/hexanes eluant) to yield 4-(benzyloxy)-6-(6-bromopyridin-2-yl)quinoline (36%). LC/MS=391.1/393.1 (M+H), LC=3.36 min.

Synthesis of 4-(benzyloxy)-6-(6-(2,6-difluorophenyl)pyridin-2-yl)quinoline

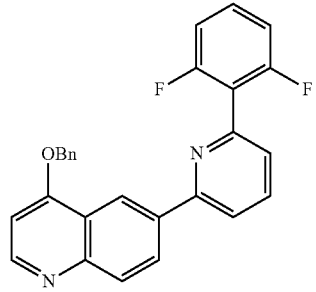 [SMILES: Fc1cccc(F)c1-c1cccc(-c2ccc3nccc(OCc4ccccc4)c3c2)n1]

A solution of 4-(benzyloxy)-6-(6-bromopyridin-2-yl)quinoline (1.0 equiv.), 2,6 difluorophenylboronic acid (3.0 equiv.), diisopropylethylamine (3.0 equiv) and tetrakis(triphenylphospine)palladium (0.1 equiv.) in 1:1 toluene/ethanol was heated in a microwave at 120° C. for 20 minutes. Upon cooling, the solution was partitioned between EtOAc and H$_2$O. Upon separation, the organic layer was washed with NaCl$_{(sat.)}$, dried over MgSO$_4$, concentrated and purified by silica gel chromatography (60-75 EtOAc/hexanes eluant) to yield 4-(benzyloxy)-6-(6-(2,6-difluorophenyl)pyridin-2-yl)quinoline (74%). LC/MS=425.1 (M+H), LC=3.59 min.

Synthesis of 6-(6-(2,6-difluorophenyl)pyridin-2-yl)quinolin-4-ol

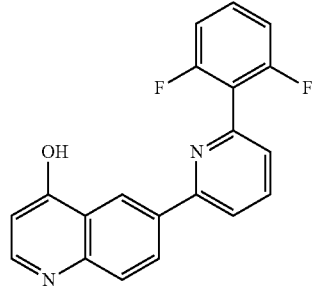 [SMILES: Oc1ccnc2ccc(-c3cccc(-c4c(F)cccc4F)n3)cc12]

To a solution of 4-(benzyloxy)-6-(6-(2,6-difluorophenyl)pyridin-2-yl)quinoline (1.0 equiv.) in 1:1 EtOH/EtOAc, at a concentration of 0.1 M, was added 10% palladium on carbon (0.1 eq.). The resultant heterogeneous solution was put under an atmosphere of hydrogen and was stirred for 72 hours. At this time the mixture was filtered through a pad of celite eluting with EtOAc. The volatiles were removed in vacuo yielding 6-(6-(2,6-difluorophenyl)pyridin-2-yl)quinolin-4-ol (70%). LCMS (m/z): 335.0 (MH$^+$); LC R$_t$=3.09 min.

Synthesis of 6-(6-(2,6-difluorophenyl)pyridin-2-yl)-quinolin-4-yl trifluoromethanesulfonate

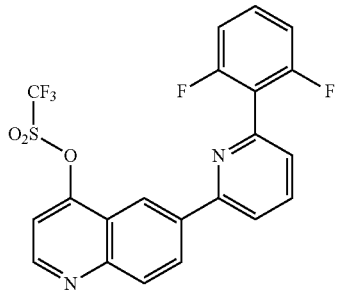 [SMILES: O=S(=O)(Oc1ccnc2ccc(-c3cccc(-c4c(F)cccc4F)n3)cc12)C(F)(F)F]

A solution of 6-(6-(2,6-difluorophenyl)pyridin-2-yl)quinolin-4-ol (1.0 equiv.), diisopropylethylamine (2.0 equiv.), and 1,1,1-trifluoro-N-phenyl-N-(trifluoromethylsulfonyl)methanesulfonamide (1.5 equiv.) in NMP (0.23 M) was stirred for 72 hours. The solution was partitioned between EtOAc and $Na_2CO_{3(sat.)}$. Upon separation, the organic layer was washed further with $Na_2CO_{3(sat.)}$ and $NaCl_{(sat.)}$, dried over $MgSO_4$, concentrated and purified by silica gel chromatography (25-35% EtOAc/hexanes eluant) to yield 6-(6-(2,6-difluorophenyl)pyridin-2-yl)quinolin-4-yl trifluoromethanesulfonate (72%). LC/MS=467.0 (M+H), LC=5.13 min.

Synthesis of trans (+/−)-Benzyl 3-(tert-butoxycarbonylamino)-4-hydroxypiperidine-1-carboxylate

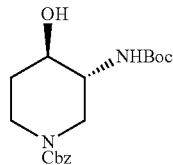 [SMILES: CC(C)(C)OC(=O)N[C@@H]1CN(C(=O)OCc2ccccc2)CC[C@H]1O]

Synthesis of trans (+/−)-Benzyl 4-(tert-butoxycarbonylamino)-3-hydroxypiperidine-1-carboxylate

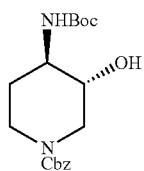

A solution of (+/−) benzyl 7-oxa-3-azabicyclo[4.1.0]heptane-3-carboxylate (1.0 equiv.) in saturated ammonium hydroxide aqueous solution and ethanol (1:1, 0.05 M solution) in a sealed steel bomb was heated to 70° C. for 5 h. After all volatile materials were removed by $N_2$ gas stream, ethyl acetate and water were added for work-up. The crude regioisomeric mixture, benzyl 3-amino-4-hydroxypiperidine-1-carboxylate and benzyl 4-amino-3-hydroxypiperidine-1-carboxylate was reacted with $Boc_2O$ (1.0 equiv.) and triethylamine (1.0 equiv.) in dichloromethane (0.1 M solution). After stirred for 2 h at room temperature, the reaction mixture was extracted with dichloromethane. The polar (+/−)-benzyl 3-(tert-butoxycarbonylamino)-4-hydroxypiperidine-1-carboxylate and nonpolar (+/−)-benzyl 4-(tert-butoxycarbonylamino)-3-hydroxypiperidine-1-carboxylate were obtained by flash column chromatography (20% to 40% EtOAc in hexanes, 28%, 51% each). LCMS (m/z): 351.1 (MH$^+$), $R_t$=0.81 min, LCMS (m/z): 351.1 (MH$^+$), $R_t$=0.83 min. The enantiomerically pure (3S,4S)-benzyl 3-(tert-butoxycarbonylamino)-4-hydroxypiperidine-1-carboxylate and (3R,4R)-benzyl 3-(tert-butoxycarbonylamino)-4-hydroxypiperidine-1-carboxylate were resolved by chiral HPLC (For analysis $R_t$=6.8 min and 9.1 min respectively; n-heptane:ethanol=70:30 (v:v), Chiralpak AD-H prep 250× 4.6 mm at 1 mL/min. For preparative separation, n-heptane:ethanol=80:20 (v:v), Chiralpak AS 50×500 mm. at 90 mL/min).

Synthesis of (3R,4R)-benzyl 3-(tert-butoxycarbonylamino)-4-(tert-butyldimethylsilyloxy)piperidine-1-carboxylate

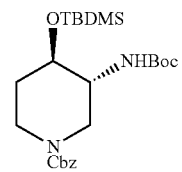 [SMILES: CC(C)(C)OC(=O)N[C@@H]1CN(C(=O)OCc2ccccc2)CC[C@H]1O[Si](C)(C)C(C)(C)C]

To a solution of (3R,4R)-benzyl 3-(tert-butoxycarbonylamino)-4-hydroxypiperidine-1-carboxylate (1.0 equiv.) in dichloromethane (0.1 M solution) was added imidazole (1.1 equiv.), DMAP (0.1 equiv.), and TBDMSCl (1.1 equiv.) sequentially. The reaction mixture was stirred at room temperature for 20 h. After worked up with dichloromethane, the crude material was purified by silica column chromatography (10% to 20% EtOAc in hexanes) yielding (3R,4R)-benzyl 3-(tert-butoxycarbonylamino)-4-(tert-butyldimethylsilyloxy)piperidine-1-carboxylate (76%). LCMS (m/z): 365.2 [(M-Boc)H$^+$]; LC $R_t$=6.05 min.

Synthesis of tert-butyl (3R,4R)-4-(tert-butyldimethylsilyloxy)piperidin-3-ylcarbamate

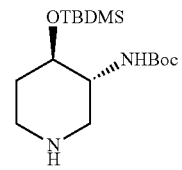 [SMILES: CC(C)(C)OC(=O)N[C@@H]1CNCC[C@H]1O[Si](C)(C)C(C)(C)C]

To a solution of (3R,4R)-benzyl 3-(tert-butoxycarbonylamino)-4-(tert-butyldimethylsilyloxy)piperidine-1-carboxylate (1.0 equiv.) in 1:1 EtOH/EtOAc, at a concentration of 0.1 M, was added 10% palladium on carbon (0.1 eq.). The resultant heterogeneous solution was put under an atmosphere of hydrogen and was stirred for 72 hours. At this time the mixture was filtered through a pad of celite eluting with EtOAc. The volatiles were removed in vacuo yielding tert- Synthesis of (3R,4R)-Benzyl 3-(tert-butoxycarbonylamino)-4-fluoropiperidine-1-carboxylate and (3S,4S)-Benzyl 3-(tert-butoxycarbonylamino)-4-fluoropiperidine-1-carboxylate

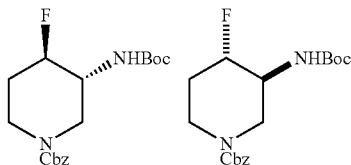 [SMILES: CC(C)(C)OC(=O)N[C@@H]1CN(C(=O)OCc2ccccc2)CC[C@H]1F ; CC(C)(C)OC(=O)N[C@H]1CN(C(=O)OCc2ccccc2)CC[C@@H]1F]

To a solution of (+/−)-benzyl 3-(tert-butoxycarbonylamino)-4-hydroxypiperidine-1-carboxylate (1.0 equiv.) in dichloromethane (0.3 M solution) was added DAST at −78° C. The reaction mixture was slowly warmed up to room temperature for 15 h. After quenched with saturated sodium bicarbonate aqueous solution, ethyl acetate and water were added for work-up. The (+/−)-benzyl 3-(tert-butoxycarbonylamino)-4-fluoropiperidine-1-carboxylate was obtained by silica column chromatography (30% EtOAc in hexanes, 40%). LCMS (m/z): 253.1 [(M-Boc)H$^+$]; LC R$_f$=4.08 min. The enantiomerically pure (3R,4R)-benzyl 3-(tert-butoxycarbonylamino)-4-fluoropiperidine-1-carboxylate and (3S,4S)-benzyl 3-(tert-butoxycarbonylamino)-4-fluoropiperidine-1-carboxylate were resolved by chiral HPLC (for analysis: R$_f$=9.4 min and 12.6 min respectively; n-heptane:isopropanol=90:10 (v:v), Chiralpak AS 250×4.6 mm at 1 mL/min. For preparative separation, n-heptane:isopropanol=90:10 (v:v), Chiralpak AS 50×500 mm. at 90 mL/min).

Synthesis of tert-butyl (3R,4R)-4-fluoropiperidin-3-ylcarbamate

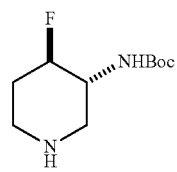 [SMILES: CC(C)(C)OC(=O)N[C@@H]1CNCC[C@H]1F]

To a solution of (3R,4R)-benzyl 3-(tert-butoxycarbonylamino)-4-fluoropiperidine-1-carboxylate (1.0 equiv.) in 1:1 EtOH/EtOAc, at a concentration of 0.1 M, was added 10% palladium on carbon (0.1 eq.). The resultant heterogeneous solution was put under an atmosphere of hydrogen and was stirred for 72 hours. At this time the mixture was filtered through a pad of celite eluting with EtOAc. The volatiles were removed in vacuo yielding tert-butyl tert-butyl (3R,4R)-4-fluoropiperidin-3-ylcarbamate (93%). LCMS (m/z): 219.2 (MH$^+$), LC R$_f$=0.45 min.

Synthesis of tert-butyl 5-methylpyridin-3-ylcarbamate

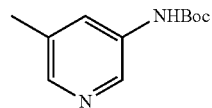

To a solution of 5-methylpyridin-3-amine (1.0 equiv.) in THF (0.5 M) at r.t. was added 1M sodium bis(trimethylsilylamide) in THF (2.2 equiv.), stirred for 15 min, followed by di-tert-butyldicarbonate (1.05 equiv.) in THF. The reaction was stirred at r.t overnight and concentrated. The concentrate was treated with 0.2M HCl (60 mL) and EtOAc, and the organic layer was extracted, washed with NaHCO$_{3(sat.)}$ and brine, dried over Na$_2$SO$_4$, filtered and concentrated. The concentrate was purified using flash chromatography on silica gel (40% EtOAc:Hexane) to give a yellow solid as product tert-butyl 5-methylpyridin-3-ylcarbamate (88%). LCMS (m/z): 209.1 (MH$^+$); LC R$_f$=1.94 min. $^1$H NMR (CDCl$_3$) δ 8.20 (d, 1H), 8.12 (s, 1H), 7.86 (s, 1H), 6.53 (s, 1H), 2.33 (s, 3H), 1.53 (s, 9H).

Synthesis of cis-(+/−)-tert-butyl 5-methylpiperidin-3-ylcarbamate

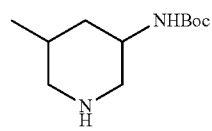

To a solution of 5-methylpyridin-3-ylcarbamate (3 g, 14 mmol) in glacial acetic Acid (50 mL) was added 5% Rhodium on active carbon (0.5 g) and Platinum(IV) oxide (0.5 g) in the hydrogenation steel bomb. The mixture was sealed and hydrogenated at 200 psi and 70° C. for 48 h. the mixture was filtered through Celite and concentrated to give cis-(+/−)-tert-butyl 5-methylpiperidin-3-ylcarbamate. LCMS (m/z): 215.1 (MH$^+$).

Method 5

Example 31

Synthesis of (3S,5R)-5-methyl-1-(6-(6-(thiazol-2-yl)-pyridin-2-yl)quinolin-4-yl)piperidin-3-amine

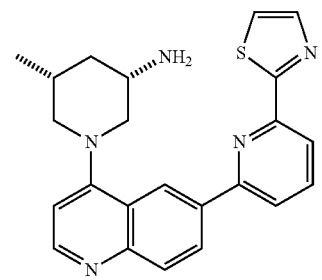 [SMILES: C[C@@H]1C[C@H](N)CN(c2ccnc3ccc(-c4cccc(-c5nccs5)n4)cc23)C1]

A solution of tert-butyl (3S,5R)-5-methylpiperidin-3-ylcarbamate (1.5 equiv.) and 6-(6-(thiazol-2-yl)pyridin-2-yl)quinolin-4-yl trifluoromethanesulfonate (1.0 equiv.) and DIEA (2.0 equiv.) in i-PrOH was heated in a microwave at 150° C. (5×20 min). Upon cooling the material was purified directly by RP-HPLC. Upon lyophilization, the Boc group was deprotected by treatment with 25% TFA/CH₂Cl₂, concentrated, purified by RP-HPLC and lyophilized to yield (3S,5R)-5-methyl-1-(6-(6-(thiazol-2-yl)pyridin-2-yl)quinolin-4-yl)piperidin-3-amine (51%). LC/MS=402.0 (M+H), LC=2.16 min.

The compounds shown in the following Table 5 were made using the procedures of the foregoing Method 5:

TABLE 5

| Example # | Structure | Compound Name | MH+ | LC Rt |
|---|---|---|---|---|
| 32 | 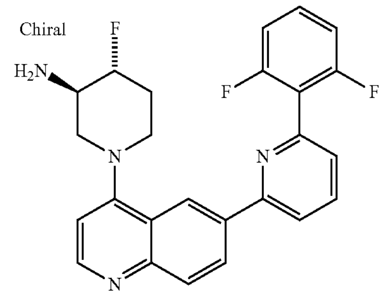 [SMILES: N[C@@H]1CN(c2ccnc3ccc(-c4cccc(-c5c(F)cccc5F)n4)cc23)CC[C@H]1F] | (3R,4R)-1-(6-(6-(2,6-difluorophenyl)pyridin-2-yl)quinolin-4-yl)-4-fluoropiperidin-3-amine | 435.3 | 2.34 |
| 33 | 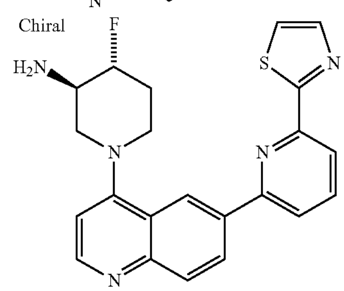 | (3R,4R)-4-fluoro-1-(6-(6-(thiazol-2-yl)pyridin-2-yl)quinolin-4-yl)piperidin-3-amine | 4.06 | 2.04 |
| 34 | 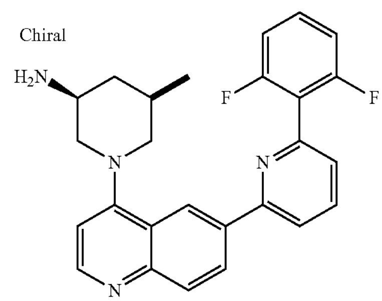 [SMILES: C[C@@H]1C[C@H](N)CN(c2ccnc3ccc(-c4cccc(-c5c(F)cccc5F)n4)cc23)C1] | (3S,5R)-1-(6-(6-(2,6-difluorophenyl)pyridin-2-yl)quinolin-4-yl)-5-methylpiperidin-3-amine | 431.3 | 2.48 |
| 35 | 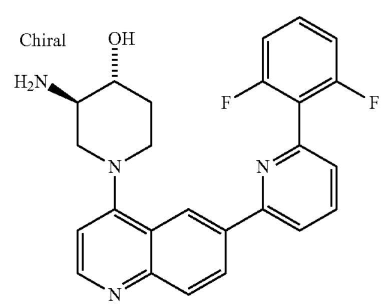 [SMILES: N[C@@H]1CN(c2ccnc3ccc(-c4cccc(-c5c(F)cccc5F)n4)cc23)CC[C@H]1O] | (3R,4R)-3-amino-1-(6-(6-(2,6-difluorophenyl)pyridin-2-yl)quinolin-4-yl)piperidin-4-ol | 433.2 | 2.23 |
| 36 | 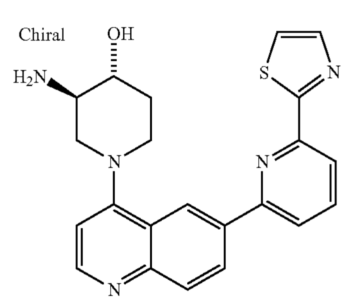 [SMILES: N[C@@H]1CN(c2ccnc3ccc(-c4cccc(-c5nccs5)n4)cc23)CC[C@H]1O] | (3R,4R)-3-amino-1-(6-(6-(thiazol-2-yl)pyridin-2-yl)quinolin-4-yl)piperidin-4-ol | 404.2 | 1.96 |

Example 37

Pim1 ATP Depletion Assay

The activity of PIM1 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 5 nM Pim1 kinase and 80 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 40 µM ATP in assay buffer is added. Final assay concentrations are 2.5 nM PIM1, 20 µM ATP, 40 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim1 ATP depletion assay and found to exhibit an $IC_{50}$ values as shown in Example 41, below. $IC_{50}$, the half maximal inhibitory concentration, represents the concentration of a test compound that is required for 50% inhibition of its target in vitro.

Example 38

Pim2 ATP Depletion Assay

The activity of PIM2 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim2 kinase and 20 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 8 µM ATP in assay buffer is added. Final assay concentrations are 5 nM PIM2, 4 µM ATP, 10 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim2 ATP depletion assay and found to exhibit an $IC_{50}$ values as shown in Example 41, below.

Example 39

Pim3 ATP Depletion Assay

The activity of PIM3 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim3 kinase and 200 µM BAD peptide (RSRHSSYPAGT-OH) in assay buffer (50 mM HEPES pH 7.5, 5 mM $MgCl_2$, 1 mM DTT, 0.05% BSA) is added into each well. After 15 minutes, 10 µl of 80 µM ATP in assay buffer is added. Final assay concentrations are 5 nM PIM1, 40 µM ATP, 100 µM BAD peptide and 2.5% DMSO. The reaction is performed until approximately 50% of the ATP is depleted, then stopped by the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim3 ATP depletion assay and found to exhibit an $IC_{50}$ values as shown in Example 41, below.

Example 40

Cell Proliferation Assay

KMS11 (human myeloma cell line), were cultured in IMDM supplemented with 10% FBS, sodium pyruvate and antibiotics. Cells were plated in the same medium at a density of 2000 cells per well into 96 well tissue culture plates, with outside wells vacant, on the day of assay. MM1.s (human myeloma cell line), were cultured in RPMI1640 supplemented with 10% FBS, sodium pyruvate and antibiotics. Cells were plated in the same medium at a density of 5000 cells per well into 96 well tissue culture plates, with outside wells vacant, on the day of assay.

Test compounds supplied in DMSO were diluted into DMSO at 500 times the desired final concentrations before dilution into culture media to 2 times final concentrations. Equal volumes of 2x compounds were added to the cells in 96 well plates and incubated at 37° C. for 3 days.

After 3 days plates were equilibrated to room temperature and equal volume of CellTiter-Glow Reagent (Promega) was added to the culture wells. The plates were agitated briefly and luminescent signal was measured with luminometer. The percent inhibition of the signal seen in cells treated with DMSO alone vs. cells treated with control compound was calculated and used to determine $EC_{50}$ values (i.e., the concentration of a test compound that is required to obtain 50% of the maximum effect in the cells) for tested compounds, as shown in Example 41.

Example 41

$IC_{50}$ and $EC_{50}$ Activity of Compounds of the Invention

Using the procedures of Examples 37 (Pim1 ATP depletion assay), 38 (Pim2 ATP depletion assay), and 39 (Pim3 ATP depletion assay), the $IC_{50}$ concentration of compounds of the previous examples were determined as shown in Table 6.

Using the procedures of Example 40 (cell proliferation assay), the $EC_{50}$ concentration of compounds of the previous examples in were determined in KMS11 cells as shown in Table 6.

TABLE 6

| | | IC50 (µM) | | | EC50 (µM) |
|---|---|---|---|---|---|
| Ex. No | Compound | PIM1 | PIM2 | PIM3 | KMS11 |
| 1 | (S)-2-(4-(3-aminopiperidin-1-yl)-3-fluoro-1,7-naphthyridin-6-yl)-6-(thiazol-2-yl)pyridin-3-amine | 0.002 | 0.04 | 0.007 | 0.87 |
| 2 | (S)-3-(5-amino-6-(4-(3-aminopiperidin-1-yl)-3-fluoro-1,7-naphthyridin-6-yl)pyridin-2-yl)-4-fluoro-N-isopropylbenzamide | 0.018 | 0.258 | 0.037 | |

TABLE 6-continued

| Ex. No | Compound | IC50 (μM) PIM1 | PIM2 | PIM3 | EC50 (μM) KMS11 |
|---|---|---|---|---|---|
| 3 | 4-(6-(3-amino-6-(2,6-difluorophenyl)pyridin-2-yl)-1,7-naphthyridin-4-yl)-6-methylpyridin-2-amine | 0.015 | 0.809 | 0.025 | |
| 4 | 3-(5-amino-6-(4-(2-amino-6-methylpyridin-4-yl)-1,7-naphthyridin-6-yl)pyridin-2-yl)-4-fluoro-N-isopropyl-benzamide | 0.024 | 0.35 | 0.04 | |
| 5 | (S)-2-(4-(3-amino-piperidin-1-yl)-1,7-naphthyridin-6-yl)-6-(thiazol-2-yl)pyridin-3-amine | 0.001 | 0.009 | 0.004 | 0.84 |
| 6 | (S)-4-(4-(3-amino-piperidin-1-yl)-1,7-naphthyridin-6-yl)-2-(2-fluorophenyl)pyrimidin-5-amine | 0.004 | 0.059 | 0.003 | 1.8 |
| 7 | (R)-2-(4-(3-amino-piperidin-1-yl)-1,7-naphthyridin-6-yl)-6-(2,6-difluorophenyl)pyridin-3-amine | 0.005 | 0.024 | 0.007 | 2.8 |
| 8 | (R)-3-(5-amino-6-(4-(3-aminopiperidin-1-yl)-1,7-naphthyridin-6-yl)pyridin-2-yl)-4-fluoro-N-isopropylbenzamide | 0.016 | 0.081 | 0.021 | 4.5 |
| 9 | (S)-2-(4-(3-amino-piperidin-1-yl)-1,7-naphthyridin-6-yl)-6-(2,6-difluorophenyl)pyridin-3-amine | 0.001 | 0.04 | 0.006 | 3.7 |
| 10 | (S)-3-(5-amino-6-(4-(3-aminopiperidin-1-yl)-1,7-naphthyridin-6-yl)pyridin-2-yl)-4-fluoro-N-isopropylbenzamide | 0.003 | 0.048 | 0.013 | 3.9 |
| 11 | (S)-2-(4-(3-amino-piperidin-1-yl)-1,7-naphthyridin-6-yl)-6-(2-fluorophenyl)pyridin-3-amine | 0.002 | 0.059 | 0.003 | 5.2 |
| 12 | (S)-3-(5-amino-6-(4-(3-aminopiperidin-1-yl)-1,7-naphthyridin-6-yl)pyridin-2-yl)-4-fluoro-N-phenylbenzamide | 0.009 | 0.098 | 0.021 | 4.1 |
| 13 | (S)-2-(4-(3-aminopiperidin-1-yl)-1,7-naphthyridin-6-yl)-6-(thiophen-2-yl)pyridin-3-amine | 0.003 | 0.054 | 0.004 | 4.7 |
| 14 | (S)-6-(4-(3-aminopiperidin-1-yl)-1,7-naphthyridin-6-yl)-6'-methoxy-2,2'-bipyridin-5-amine | 0.006 | 0.132 | 0.008 | |
| 15 | (S)-3-(5-amino-6-(4-(3-aminopiperidin-1-yl)-1,7-naphthyridin-6-yl)pyridin-2-yl)-N-cyclohexyl-4-fluorobenzamide | 0.009 | 0.074 | 0.022 | 3.1 |
| 16 | (S)-3-(5-amino-6-(4-(3-aminopiperidin-1-yl)-1,7-naphthyridin-6-yl)pyridin-2-yl)-4-fluoro-N,N-dimethylbenzamide | 0.01 | 0.12 | 0.041 | 4 |
| 17 | (S)-2-(4-(3-aminopiperidin-1-yl)-1,7-naphthyridin-6-yl)-6-(2,4-difluorophenyl)pyridin-3-amine | 0.004 | 0.151 | 0.013 | |
| 18 | (S)-2-(4-(3-aminopiperidin-1-yl)-1,7-naphthyridin-6-yl)-6-(2,3-difluorophenyl)pyridin-3-amine | 0.002 | 0.071 | 0.004 | 4.9 |
| 19 | (S)-2-(4-(3-aminopiperidin-1-yl)-1,7-naphthyridin-6-yl)-6-(4-fluorophenyl)pyridin-3-amine | 0.006 | 0.102 | 0.007 | 4 |
| 20 | (S)-2-(4-(3-aminopiperidin-1-yl)-1,7-naphthyridin-6-yl)-6-phenylpyridin-3-amine | 0.003 | 0.062 | 0.004 | 4.2 |
| 21 | (S)-3-(5-amino-6-(4-(3-aminopiperidin-1-yl)-1,7-naphthyridin-6-yl)pyridin-2-yl)benzenesulfonamide | 0.002 | 0.16 | 0.008 | |
| 22 | (S)-2-(4-(3-aminopiperidin-1-yl)-1,7-naphthyridin-6-yl)-6-(3-(methylsulfonyl)phenyl)pyridin-3-amine | 0.004 | 0.28 | 0.01 | |
| 23 | (S)-4-(5-amino-6-(4-(3-aminopiperidin-1-yl)-1,7-naphthyridin-6-yl)pyridin-2-yl)benzenesulfonamide | 0.002 | 0.034 | 0.007 | 7.8 |
| 24 | (S)-2-(4-(3-aminopiperidin-1-yl)-1,7-naphthyridin-6-yl)-6-(4-(methylsulfonyl)phenyl)pyridin-3-amine | 0.002 | 0.034 | 0.007 | 1.2 |
| 25 | (S)-1-(6-(6-(thiazol-2-yl)pyridin-2-yl)-1,7-naphthyridin-4-yl)piperidin-3-amine | 0.006 | 0.06 | 0.007 | 0.59 |
| 26 | (S)-1-(6-(6-(2,6-difluorophenyl)pyridin-2-yl)quinolin-4-yl)piperidin-3-amine | 0.016 | 0.331 | 0.026 | |
| 27 | (S)-1-(6-(6-(thiazol-2-yl)pyridin-2-yl)quinolin-4-yl)piperidin-3-amine | 0.01 | 0.045 | 0.01 | 0.94 |
| 28 | (S)-1-(6-(4-(thiazol-2-yl)pyrimidin-2-yl)quinolin-4-yl)piperidin-3-amine | 0.007 | 0.068 | 0.007 | 0.77 |
| 29 | (S)-1-(6-(4-(2-fluorophenyl)pyrimidin-2-yl)quinolin-4-yl)piperidin-3-amine | 0.006 | 0.132 | 0.008 | |
| 30 | (S)-1-(6-(4-(2,6-difluorophenyl)pyrimidin-2-yl)quinolin-4-yl)piperidin-3-amine | 0.008 | 0.347 | 0.02 | |
| 31 | (3S,5R)-5-methyl-1-(6-(6-(thiazol-2-yl)pyridin-2-yl)quinolin-4-yl)piperidin-3-amine | 0.005 | 0.012 | 0.006 | 0.79 |
| 32 | (3R,4R)-1-(6-(6-(2,6-difluorophenyl)pyridin-2-yl)quinolin-4-yl)-4-fluoropiperidin-3-amine | 0.027 | 0.604 | 0.042 | |
| 33 | (3R,4R)-4-fluoro-1-(6-(6-(thiazol-2-yl)pyridin-2-yl)quinolin-4-yl)piperidin-3-amine | 0.022 | 0.244 | 0.021 | |

TABLE 6-continued

| Ex. No | Compound | IC50 (µM) PIM1 | PIM2 | PIM3 | EC50 (µM) KMS11 |
|---|---|---|---|---|---|
| 34 | (3S,5R)-1-(6-(6-(2,6-difluorophenyl)pyridin-2-yl)quinolin-4-yl)-5-methylpiperidin-3-amine | 0.002 | 0.033 | 0.007 | |
| 35 | (3R,4R)-3-amino-1-(6-(6-(2,6-difluorophenyl)pyridin-2-yl)quinolin-4-yl)piperidin-4-ol | 0.019 | 0.373 | 0.021 | |
| 36 | (3R,4R)-3-amino-1-(6-(6-(thiazol-2-yl)pyridin-2-yl)quinolin-4-yl)piperidin-4-ol | 0.009 | 0.075 | 0.009 | |

While illustrative embodiments have been illustrated and described, it will be appreciated that various changes can be made therein without departing from the spirit and scope of the invention.

The invention claimed is:
1. A compound of Formula I,

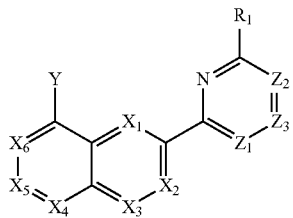

I or a stereoisomer, tautomer, or pharmaceutically acceptable salt thereof, wherein, $X_2$, and $X_4$ are N, and $X_1$, $X_3$, $X_5$, and $X_6$ are $CR_2$;
or $X_4$ is N and $X_1$, $X_2$, $X_3$, $X_5$, and $X_6$ are $CR_2$;

Y is selected from a group consisting of piperidinyl, piperazinyl, cyclohexyl, pyrimidyl, and pyrazinyl, wherein each member of the group is substituted with up to four substituents; $Z_1$, $Z_2$, and $Z_3$ are each $CR_{12}$;

$R_1$ is selected from the group consisting of halo, and substituted or unsubstituted alkyl, alkenyl, alkynyl, alkoxy, amino, cycloalkyl, hetero cycloalkyl, aryl, heteroaryl, aryloxy, heteroaryloxy, heterocyclyloxy, cycloalkyloxy, acyl, acylamino and acyloxy, and partially saturated cycloalkyl; and $R_2$ and $R_{12}$ independently at each occurrence are selected from the group consisting of hydrogen, halo, hydroxyl, and substituted or unsubstituted alkyl, alkenyl, alkynyl, alkoxy, amino, cycloalkyl, hetero cycloalkyl, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, aryloxy, heteroaryloxy, heterocyclyloxy, cycloalkyloxy, acyl, acylamino and acyloxy, and partially saturated cycloalkyl.

2. A compound of claim 1, wherein Y is substituted piperidinyl, substituted cyclohexyl, or substituted piperazinyl.

3. A compound of claim 2 wherein Y is substituted piperidinyl or substituted cyclohexyl.

4. A compound of claim 3 wherein $R_{12}$ is selected from amino, hydrogen and halo.

5. A compound selected from the group consisting of (S)-2-(4-(3-aminopiperidin-1-yl)-3-fluoro-1,7-naphthyridin-6-yl)-6-(thiazol-2-yl)pyridin-3-amine, (S)-3-(5-amino-6-(4-(3-aminopiperidin-1-yl)-3-fluoro-1,7-naphthyridin-6-yl)pyridin-2-yl)-4-fluoro-N-isopropylbenzamide, 4-(6-(3-amino-6-(2,6-difluorophenyl)pyridin-2-yl)-1,7-naphthyridin-4-yl)-6-methylpyridin-2-amine, 3-(5-amino-6-(4-(2-amino-6-methylpyridin-4-yl)-1,7-naphthyridin-6-yl)pyridin-2-yl)-4-fluoro-N-isopropyl-benzamide, (S)-2-(4-(3-aminopiperidin-1-yl)-1,7-naphthyridin-6-yl)-6-(thiazol-2-yl)pyridin-3-amine, (R)-2-(4-(3-aminopiperidin-1-yl)-1,7-naphthyridin-6-yl)-6-(2,6-difluorophenyl)-pyridin-3-amine, (R)-3-(5-amino-6-(4-(3-aminopiperidin-1-yl)-1,7-naphthyridin-6-yl)pyridin-2-yl)-4-fluoro-N-isopropylbenzamide, (S)-2-(4-(3-aminopiperidin-1-yl)-1,7-naphthyridin-6-yl)-6-(2,6-difluorophenyl)pyridin-3-amine, (S)-3-(5-amino-6-(4-(3-aminopiperidin-1-yl)-1,7-naphthyridin-6-yl)pyridin-2-yl)-4-fluoro-N-isopropylbenzamide, (S)-2-(4-(3-aminopiperidin-1-yl)-1,7-naphthyridin-6-yl)-6-(2-fluorophenyl)pyridin-3-amine, (S)-3-(5-amino-6-(4-(3-aminopiperidin-1-yl)-1,7-naphthyridin-6-yl)pyridin-2-yl)-4-fluoro-N-phenylbenzamide, (S)-2-(4-(3-aminopiperidin-1-yl)-1,7-naphthyridin-6-yl)-6-(thiophen-2-yl)pyridin-3-amine, (S)-6-(4-(3-aminopiperidin-1-yl)-1,7-naphthyridin-6-yl)-6'-methoxy-2,2'-bipyridin-5-amine, (S)-3-(5-amino-6-(4-(3-aminopiperidin-1-yl)-1,7-naphthyridin-6-yl)pyridin-2-yl)-N-cyclohexyl-4-fluorobenzamide, (S)-3-(5-amino-6-(4-(3-aminopiperidin-1-yl)-1,7-naphthyridin-6-yl)pyridin-2-yl)-4-fluoro-N,N-dimethylbenzamide, (S)-2-(4-(3-aminopiperidin-1-yl)-1,7-naphthyridin-6-yl)-6-(2,4-difluorophenyl)pyridin-3-amine, (S)-2-(4-(3-aminopiperidin-1-yl)-1,7-naphthyridin-6-yl)-6-(2,3-difluorophenyl)pyridin-3-amine, (S)-2-(4-(3-aminopiperidin-1-yl)-1,7-naphthyridin-6-yl)-6-(4-fluorophenyl)pyridin-3-amine, (S)-2-(4-(3-aminopiperidin-1-yl)-1,7-naphthyridin-6-yl)-6-phenylpyridin-3-amine, (S)-3-(5-amino-6-(4-(3-aminopiperidin-1-yl)-1,7-naphthyridin-6-yl)pyridin-2-yl)benzenesulfonamide, (S)-2-(4-(3-aminopiperidin-1-yl)-1,7-naphthyridin-6-yl)-6-(3-(methylsulfonyl)phenyl)pyridin-3-amine, (S)-4-(5-amino-6-(4-(3-aminopiperidin-1-yl)-1,7-naphthyridin-6-yl)pyridin-2-yl)benzenesulfonamide, (S)-2-(4-(3-aminopiperidin-1-yl)-1,7-naphthyridin-6-yl)-6-(4-(methylsulfonyl)phenyl)pyridin-3-amine, and (S)-1-(6-(6-(thiazol-2-yl)pyridin-2-yl)-1,7-naphthyridin-4-yl)piperidin-3-amine.

6. A compound of claim 1 having the following Formula II,

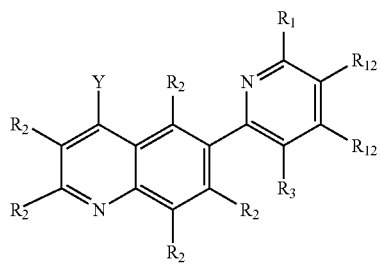

II or a stereoisomer, tautomer, or pharmaceutically acceptable salt thereof, wherein, Y is selected from a group consisting of substituted or unsubstituted cyclohexyl, piperidinyl, and piperazinyl; wherein each member of the group is substituted with up to four substituents;

$R_1$ is selected from the group consisting of unsubstituted and substituted aryl, heteroaryl, alkyl, cycloalkyl, and halo;

$R_3$ is selected form hydrogen, halo, CN, $NH_2$, $C_{1-4}$ alkyl and $C_{3-4}$ cycloalkyl; and each $R_2$ and $R_{12}$ independently at each occurrence is selected from the group consisting of hydrogen, halo, hydroxyl, and substituted or unsubstituted alkyl, alkenyl, alkynyl, alkoxy, amino, cycloalkyl, hetero cycloalkyl, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, aryloxy, heteroaryloxy, heterocyclyloxy, cycloalkyloxy, acyl, acylamino and acyloxy, and partially saturated cycloalkyl.

7. A compound of claim 1 having the following Formula IV,

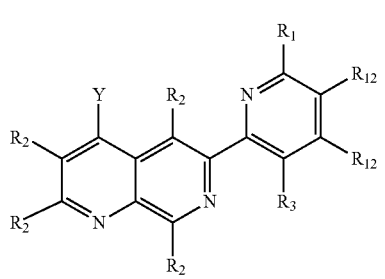

or a stereoisomer, tautomer, or pharmaceutically acceptable salt thereof, wherein, Y is selected from a group consisting of substituted or unsubstituted cyclohexyl, piperidinyl, and piperazinyl;

$R_1$ is selected from the group consisting of unsubstituted and substituted aryl, heteroaryl, alkyl, cycloalkyl, and halo;

$R_3$ is selected from hydrogen, halo, CN, $NH_2$, $C_{1-4}$ alkyl and $C_{3-4}$ cycloalkyl; and $R_2$ and $R_{12}$ independently at each occurrence are selected from the group consisting of hydrogen, halo, hydroxyl, and substituted or unsubstituted alkyl, alkenyl, alkynyl, alkoxy, amino, cycloalkyl, hetero cycloalkyl, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, aryloxy, heteroaryloxy, heterocyclyloxy, cycloalkyloxy, acyl, acylamino and acyloxy, and partially saturated cycloalkyl.

8. A compound of claim 1,
which has the Formula II or IV:

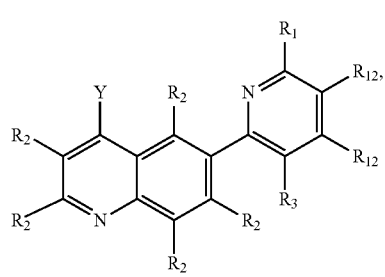

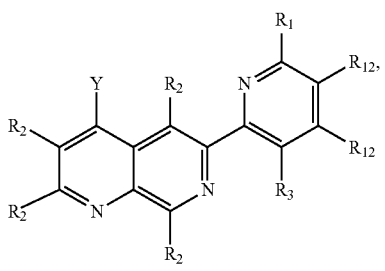

wherein,

Y is as defined in claim 1;

$R_1$ is selected from the group consisting of substituted or unsubstituted alkyl, cycloalkyl, heterocycloalkyl, aryl and heteroaryl;

$R_2$ and $R_{12}$ independently at each occurrence are selected from the group consisting of hydrogen, halo, hydroxyl, and substituted or unsubstituted alkyl, alkenyl, alkynyl, alkoxy, amino, cycloalkyl, hetero cycloalkyl, aminocarbonyloxy, aminosulfonyl, aminosulfonyloxy, aminosulfonylamino, amidino, carboxyl, carboxyl ester, (carboxyl ester)amino, (carboxyl ester)oxy, sulfonyl, sulfonyloxy, thioacyl, thiol, alkylthio, aryl, heteroaryl, aryloxy, heteroaryloxy, heterocyclyloxy, cycloalkyloxy, acyl, acylamino and acyloxy, and partially saturated cycloalkyl; and $R_3$ is selected from the group consisting of hydrogen, $C_{1-6}$ alkyl, halo and amino.

9. A compound of claim 1, selected from the group consisting of (S)-1-(6-(6-(2,6-difluorophenyl)pyridin-2-yl)quinolin-4-yl)piperidin-3-amine, (S)-1-(6-(6-(thiazol-2-yl)pyridin-2-yl)quinolin-4-yl)piperidin-3-amine, (3S,5R)-5-methyl-1-(6-(6-(thiazol-2-yl)pyridin-2-yl)quinolin-4-yl)piperidin-3-amine, (3R,4R)-1-(6-(6-(2,6-difluorophenyl)pyridin-2-yl)quinolin-4-yl)-4-fluoropiperidin-3-amine, (3R,4R)-4-fluoro-1-(6-(6-(thiazol-2-yl)pyridin-2-yl)quinolin-4-yl)piperidin-3-amine, (3S,5R)-1-(6-(6-(2,6-difluorophenyl)pyridin-2-yl)quinolin-4-yl)-5-methylpiperidin-3-amine, (3R,4R)-3-amino-1(6-(6-(2,6-difluorophenyl)pyridin-2-yl)quinolin-4-yl)piperidin-4-ol, and (3R,4R)-3-amino-1-(6-(6-(thiazol-2-yl)pyridin-2-yl)quinolin-4-yl)piperidin-4-ol.

10. The compound of claim 1, or a stereoisomer, tautomer, or pharmaceutically acceptable salt thereof, wherein, Y is selected from a group consisting of piperidinyl, piperazinyl, and cyclohexyl, wherein each member of the group is substituted with up to four substituents selected from hydroxy, amino, cyano, halo loweralkyl, haloloweralkyl, and loweralkoxy; $R_1$ is selected from the group consisting of substituted or unsubstituted cycloalkyl, hetero cycloalkyl, aryl, heteroaryl, and partially saturated cycloalkyl; and $R_2$ and $R_{12}$ independently at each occurrence are selected from the group consisting of hydrogen, halo, hydroxyl, and unsubstituted alkyl, alkoxy, or amino.

11. The compound of claim 10, wherein $R_1$ is selected from the group consisting of substituted or unsubstituted aryl and heteroaryl, optionally substituted with one or more groups selected from hydroxy, amino, cyano, halo loweralkyl, haloloweralkyl, and loweralkoxy.

12. A pharmaceutical composition comprising an effective amount of a compound of claim 1.

13. A pharmaceutical composition comprising an effective amount of a compound of claim 8.

14. A method for inhibiting PIM kinase activity in a cell, comprising contacting the cell with an effective amount of a compound of claim 1.

15. A method for inhibiting PIM kinase activity in a cell, comprising contacting the cell with an effective amount of a compound of claim 8.

16. A method for treating multiple myeloma, comprising administering to a patient in need of such treatment an effective amount of a compound of claim 1.

17. A method for treating multiple myeloma, comprising administering to a patient in need of such treatment an effective amount of a compound of claim 8.

* * * * *